United States Patent
Sweitzer

(10) Patent No.: US 10,772,739 B2
(45) Date of Patent: Sep. 15, 2020

(54) ACETABULAR CUP EXTRACTOR

(71) Applicant: Shukla Medical, St. Petersburg, FL (US)

(72) Inventor: Zachary Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 245 days.

(21) Appl. No.: 16/038,570

(22) Filed: Jul. 18, 2018

(65) Prior Publication Data

US 2019/0021879 A1 Jan. 24, 2019

Related U.S. Application Data

(60) Provisional application No. 62/681,468, filed on Jun. 6, 2018, provisional application No. 62/534,902, filed on Jul. 20, 2017.

(51) Int. Cl.
*A61F 2/46* (2006.01)

(52) U.S. Cl.
CPC .......... *A61F 2/4609* (2013.01); *A61F 2/4603* (2013.01); *A61F 2002/4619* (2013.01); *A61F 2002/4681* (2013.01)

(58) Field of Classification Search
CPC ........ A61F 2/46; A61F 2/4603; A61F 2/4609; A61F 2002/4619; A61F 2002/4625; A61F 2002/4681
See application file for complete search history.

(56) References Cited

U.S. PATENT DOCUMENTS 6,565,575 B2 * 5/2003 Lewis .................. A61F 2/4609
606/99
6,565,757 B1 5/2003 Wedkamp
(Continued)

FOREIGN PATENT DOCUMENTS

WO 2014063197 A1 5/2014
WO 2015155657 A1 10/2015
(Continued)

OTHER PUBLICATIONS

EPO Examination Report dated Dec. 19, 2019 in European Patent Application No. 18184404.4.
(Continued)

*Primary Examiner* — Eric S Gibson
(74) *Attorney, Agent, or Firm* — Kim IP Law Group PLLC

(57) ABSTRACT

An orthopedic instrument in the form of an acetabular cup extractor system for reliably and efficiently extracting an acetabular cup implant from an acetabulum. The system includes a handle assembly, an extractor attachable to a distal end of the handle, and a dome guide assembly having a hemi-spherical dome for engaging the extractor and a centering body extending distally from the hemi-spherical dome for engaging an acetabular implant. The extractor includes a curved, concave guide and a curved blade. The curved, concave guide is sized and shaped to substantially matingly engage with and cover a substantial portion of the hemi-spherical dome. As a result of such an arrangement, a uniform cut is achieved by the curved blade thereby resulting in a minimum of bone being extracted from the acetabulum around the acetabular cup implant during a surgical procedure.

22 Claims, 20 Drawing Sheets

(56) References Cited

U.S. PATENT DOCUMENTS

| | | | |
|---|---|---|---|
| 7,744,602 B2* | 6/2010 | Teeny | A61F 2/4609 |
| | | | 606/100 |
| 7,763,031 B2* | 7/2010 | Tulkis | A61B 17/1666 |
| | | | 606/81 |
| 9,931,225 B2* | 4/2018 | Hudak, Jr. | A61F 2/4609 |
| 2002/0116007 A1* | 8/2002 | Lewis | A61F 2/4609 |
| | | | 606/99 |
| 2006/0195105 A1* | 8/2006 | Teeny | A61F 2/4609 |
| | | | 606/76 |
| 2006/0200165 A1* | 9/2006 | Tulkis | A61B 17/1666 |
| | | | 606/99 |
| 2007/0010825 A1 | 1/2007 | Leisinger et al. | |
| 2008/0195111 A1* | 8/2008 | Anderson | A61F 2/4609 |
| | | | 606/90 |
| 2012/0184964 A1* | 7/2012 | Hudak, Jr. | A61F 2/4609 |
| | | | 606/91 |
| 2015/0313722 A1* | 11/2015 | Hudak, Jr. | A61F 2/4609 |
| | | | 606/99 |
| 2016/0100957 A1* | 4/2016 | Lewis | A61F 2/4609 |
| | | | 606/84 |
| 2019/0021879 A1* | 1/2019 | Sweitzer | A61F 2/4609 |

FOREIGN PATENT DOCUMENTS

| | | |
|---|---|---|
| WO | 2017019332 A1 | 2/2017 |
| WO | 2017180602 A1 | 10/2017 |

OTHER PUBLICATIONS

International Search Report in PCT Application No. PCT/US2017/026975 dated Jul. 18, 2017.

Written Opinion in PCT Application No. PCT/US2017/026975 dated Jul. 18, 2017.

European Search Report in European Application No. EP18184404, dated Oct. 16, 2018.

* cited by examiner

ACETABULAR CUP EXTRACTOR

CROSS-REFERENCE TO RELATED APPLICATIONS

This application claims the benefit of U.S. Provisional Application No. 62/534,902 filed Jul. 20, 2017 entitled "Acetabular Cup Extractor" and of U.S. Provisional Application No. 62/681,468 filed Jun. 6, 2018 entitled "Acetabular Cup Extractor," the disclosures of which are incorporated by reference herein in their entirety for all purposes.

BACKGROUND

The exemplary embodiments of present invention relate generally to an orthopedic instrument and, more specifically, to an acetabular cup extractor.

In performing hip orthoplasty surgery, an acetabular cup implant is installed in the hip socket or acetabulum. When installing the acetabular cup implant into the acetabulum, bone is removed from the acetabulum to receive the acetabular cup implant and the acetabular cup implant is attached, e.g., with cement, bone screws or press-fitted. The acetabular cup implant may have a porous, typically metal coating shell which surrounds a liner adapted to receive the ball-like head of a hip stem implant. Bone gradually grows onto and/or into the porous metal shell to permanently affix the acetabular cup implant to the acetabulum.

Prosthetic hip joints, like their natural counterparts, experience wear over time. When a prosthetic hip joint becomes worn or damaged to a point necessitating maintenance or replacement, the acetabular cup implant may have to be replaced. In order to replace the acetabular cup implant, an extractor is used to extract the existing acetabular cup implant from the acetabulum.

Among the disadvantages of conventional extractors is that the blades are either permanently attached to the handle or attached with a threaded fastener which actions may prolong surgery time. Conventional extractors have blades with flat cutting edges which require substantial force to plunge the blades into the bone surrounding the acetabular cup implant being extracted. Handles of typical extractors also are not ergonomically shaped which render them uncomfortable to the user because of the substantial force that must be applied to the handle during use. Conventional extractors also typically have a single impact surface to dislodge the blade in the event it gets stuck in the bone, which may not be optimally positioned for striking.

In addition, in conventional extraction systems having a spherical head that caps an implant the spherical head can easily separate from the acetabular cup liner when the handle is used to drive the blade into bone, e.g., by being struck by a hammer. Such separation of the spherical head detrimentally impacts the user's ability to control the point of insertion of the blade into bone. As a consequence, the blade may make an irregular cut of the surrounding bone whereby more bone than necessary may be cut in order to extract the acetabular cup from the acetabulum. In revision surgery to remove existing implants, as little bone as possible should be removed from around the acetabular cup in order to preserve the integrity of the surrounding bone.

BRIEF SUMMARY OF THE DISCLOSURE

In accordance with an exemplary embodiment there is provided an acetabular cup extractor system comprising a handle, an extractor, and a dome guide assembly. The handle includes an elongated shaft and a transverse handle extending substantially transverse to a longitudinal axis of the elongated shaft. The extractor is attachable to a distal end of the handle. The extractor includes a guide and a blade. The dome guide assembly includes a hemi-spherical dome for engaging the extractor and a centering body extending distally from the hemi-spherical dome for engaging an acetabular implant.

An aspect of the exemplary embodiment is that the elongated shaft includes a strike plate about its proximal end. Further, the transverse handle includes a first gripping handle at a first end of the transverse handle and a second gripping handle at a second end of the transverse handle opposite the first end. The first gripping handle has a longitudinal axis that extends transverse to a longitudinal axis of the second gripping handle, and the second gripping handle includes a distally facing planar strike plate.

Another aspect of the exemplary embodiment is that the first gripping handle has a longitudinal axis substantially parallel to a longitudinal axis of the elongated shaft and the elongated shaft includes a fastener about its distal end for connecting to the extractor.

Another aspect of the exemplary embodiment is that the guide is a curved guide or a concave shaped guide.

Another aspect of the exemplary embodiment is that the blade is a curved blade. The blade can be curved in both its longitudinal direction and in a widthwise extent transverse to the longitudinal direction. In an aspect, a tangency of a surface of a base of the blade is at a non-zero angle relative to a longitudinal axis of the elongated shaft. In an aspect, a portion of the blade extends beyond a plane defined by a side of the elongated shaft.

Another aspect of the exemplary embodiment is that the extractor includes a mount for engaging a fastener of the elongated shaft. In an aspect, the guide extends from the mount and the blade extends from the mount in a direction opposite the guide.

Another aspect of the exemplary embodiment is that the hemi-spherical dome includes a circular mount and a polymeric dome-like cap mounted to the circular mount. The circular mount includes a post and the polymeric dome-like cap includes a through hole for receiving the post. Further, the polymeric dome-like cap has an overall width greater than an overall width of the circular mount. The polymeric dome-like cap has an overall height greater than an overall height of the post. Additionally, the post includes a fastener for connecting with the centering body.

Another aspect of the exemplary embodiment is that the centering body includes a sphere-like body and a fastener extending from the sphere-like body for connecting with the hemi-spherical dome. The centering body further includes a pair of flats at its lateral sides.

Another aspect of the exemplary embodiment is that the system further comprises a second extractor attachable to the distal end of the handle assembly. The second extractor includes a finishing guide and a finishing blade having an overall length greater than the blade of the extractor.

Another aspect of the exemplary embodiment is that there is provided a handle assembly for an orthopedic instrument comprising an elongated shaft and a lever assembly. The elongated shaft includes a distal end for engaging a tool and a proximal end having an impact surface. The lever assembly extends substantially transverse to a longitudinal axis of the elongated shaft. The lever assembly includes a first handle extending away from a first lateral side of the elongated shaft, and a second handle extending away from a second lateral side of the elongated shaft opposite the first lateral side.

Another aspect of the exemplary embodiment is that the impact surface is a proximally facing strike plate. In addition, the strike plate includes an overall width larger than an overall width of the elongated shaft. The distal end includes a detent for engaging a cooperating detent of the tool. The lever assembly is attached to the elongated shaft adjacent the proximal end of the elongated shaft. The first handle includes a longitudinal axis that extends transverse to a longitudinal axis of the second handle and includes a striking surface on its undersurface or distal end. The second handle includes a center that is spaced further from a longitudinal axis of the elongated shaft than a center of the first handle. The second handle includes a planar strike plate. The planar strike plate is a distally facing strike plate. The elongated shaft has an overall length greater than an overall longitudinal length of the lever assembly. The elongated shaft has an overall length substantially the same as an overall longitudinal length of the lever assembly. Further, the elongated shaft has a length of about 6 to about 30 inches. The handle assembly comprises a mass of about 1 to 2 lbs. A mass of the lever assembly about the first lateral side of the elongated shaft is substantially the same as a mass of the lever assembly about the second lateral side.

Another aspect of the exemplary embodiment is that there is provided an extractor for an orthopedic instrument comprising a hub, a hemi-spherical shell-like guide and a blade. The hub engages a handle. The hemi-spherical shell-like guide extends from the hub. The blade extends from one of the hub and the hemi-spherical shell-like guide.

Another aspect of the exemplary embodiment is that the hub extends from the hemi-spherical shell-like guide such that a longitudinal axis of the hub extends through a circle defined by an arc of an outer surface of the hemi-spherical shell-like guide in a chord-like fashion. Further, the hub includes a detent for engaging a cooperating detent on a tool. The blade is an arcuate shaped blade. The blade is curved in both its longitudinal direction and in a widthwise extent transverse to the longitudinal direction. The blade includes a point directed substantially distally from the hub. The blade extends along a path defined by an arc path of the hemi-spherical shell-like guide. The blade extends substantially distally from a longitudinal axis of the hub an arc of about 90 degrees. The blade extends substantially distally from a longitudinal axis of the hub an arc of about 45-80 degrees. The blade is positioned centrally between opposing ends of the hemi-spherical shell-like guide. A portion of the blade extends beyond a plane defined by a side of the hub. A tangency of a surface of a base of the blade is at a non-zero angle relative to a longitudinal axis of the hub. A point of the blade extends to about a most distal point of the hemi-spherical shell-like guide. A point of the blade extends beyond a most distal point of the hemi-spherical shell-like guide. The hemi-spherical shell-like guide extends a revolution of about 180 degrees relative to a central axis of the hemi-spherical shell-like guide. The hemi-spherical shell-like guide extends distally from the hub an arc of about 90 degrees. The hemi-spherical shell-like guide extends distally from the hub an arc of about 45-80 degrees.

Another aspect of the exemplary embodiment is that there is provided a guide assembly for an orthopedic instrument comprising a hemi-spherical dome assembly and a spherical-like centering body extending distally from the hemi-spherical dome assembly for engaging an implant. The spherical-like centering body is sized and shaped to be received within and engaging an acetabular implant. The hemi-spherical dome assembly includes a circular mount and a dome-like cap mounted to the circular mount. The dome-like cap is polymeric, or metallic with a low-friction coating. The circular mount includes a post and the post includes a fastener. Additionally, the post includes threads for engaging the spherical-like centering body. The circular mount includes an undercut relief. The circular mount includes a skirt having a spherical shell-like curvature. The skirt includes a plurality of spaced apart cutouts and/or a plurality of spaced apart legs. The polymeric dome-like cap includes a through hole for receiving the circular mount. The polymeric dome-like cap has an overall width greater than an overall width of the circular mount and/or an overall height greater than an overall height of the post. The spherical-like centering body includes a sphere-like body and a mounting member extending from the sphere-like body for connecting with the hemi-spherical dome assembly. The spherical-like centering body includes a pair of flats on its lateral sides. The sphere-like body includes a pair of flats on its lateral sides.

In accordance with the exemplary embodiment, there is provided an orthopedic instrument in the form of an acetabular cup extractor system for reliably and efficiently extracting an acetabular cup implant from an acetabulum. The system includes a tool in the form of a handle assembly, another tool in the form of an extractor attachable to a distal end of the handle assembly, and a dome guide assembly having a hemi-spherical dome for engaging the extractor and a centering body extending distally from the hemi-spherical dome for engaging an acetabular implant. The extractor includes a curved, concave guide and a curved blade. The curved, concave guide is sized and shaped to substantially matingly engage with and cover a substantial portion of the hemi-spherical dome. In this way, when a user strikes the handle assembly with a hammer or similar tool, the downwardly directed impact force transferred by the handle assembly causes the mating engagement surfaces of the curved, concave guide and the hemi-spherical dome to remain in contact with each other, and the centering body and the acetabular implant to remain in contact with each other, as the curved blade is driven into the bone surrounding the acetabular cup implant. As a result of such an arrangement, a uniform cut is achieved by the curved blade thereby resulting in a minimum of bone being extracted from the acetabulum around the acetabular cup implant during the surgical procedure.

Other features and advantages of the subject disclosure will be apparent from the following more detail description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

DETAILED DESCRIPTION OF THE DISCLOSURE

Figure 1:
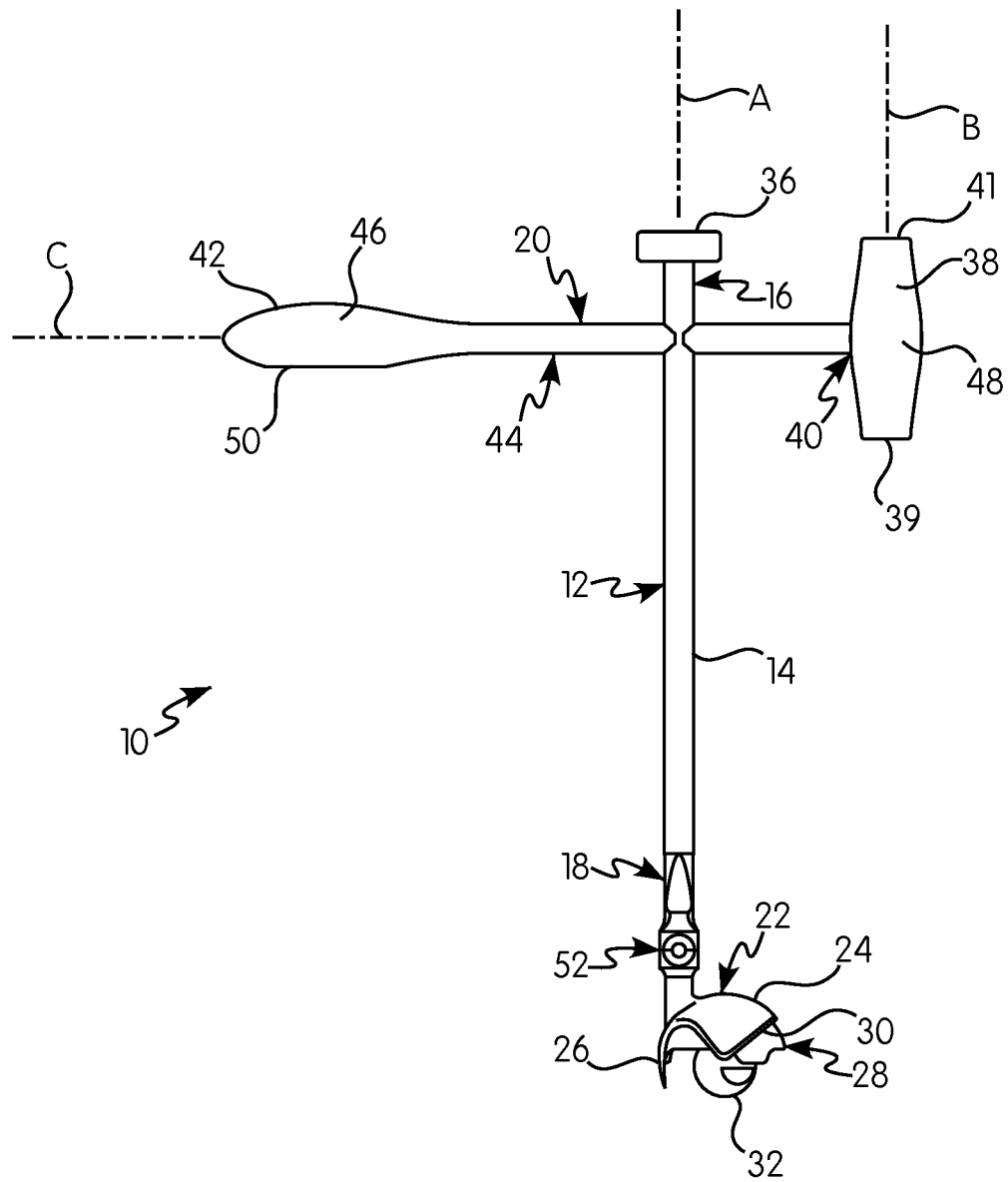
FIG. 1 is a left-side elevational view of an acetabular cup extractor system in accordance with an exemplary embodiment of the subject disclosure.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 2:
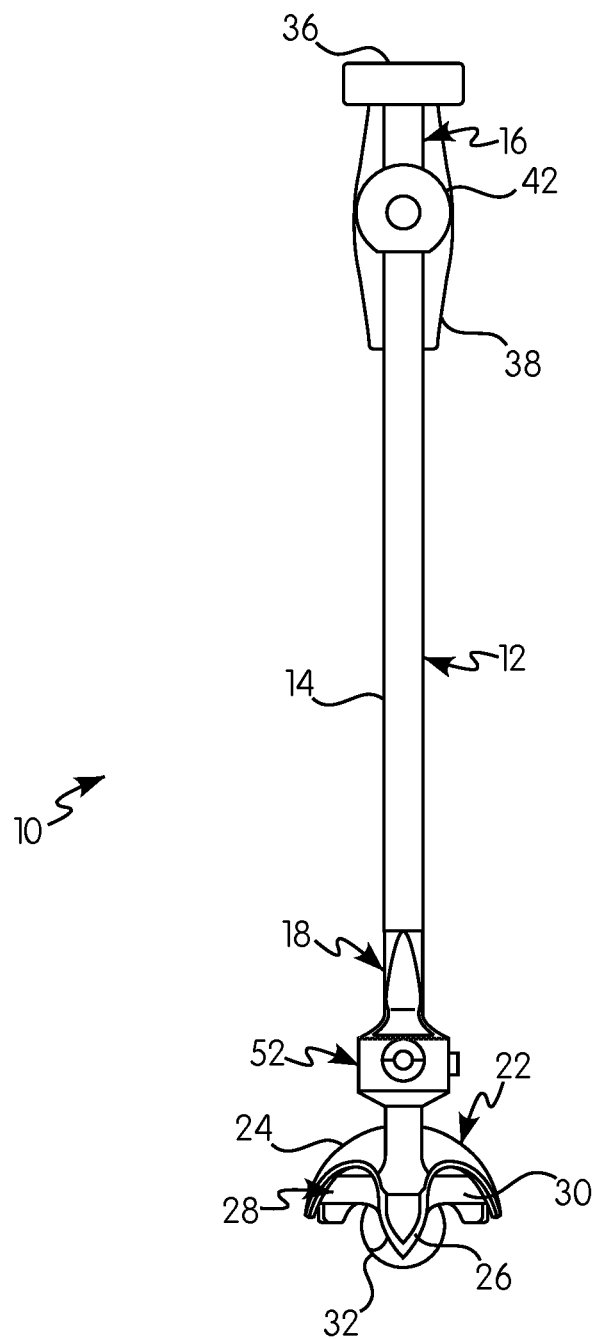
FIG. 2 is a front elevational view of the acetabular cup extractor system of FIG. 1.
Figure 3:
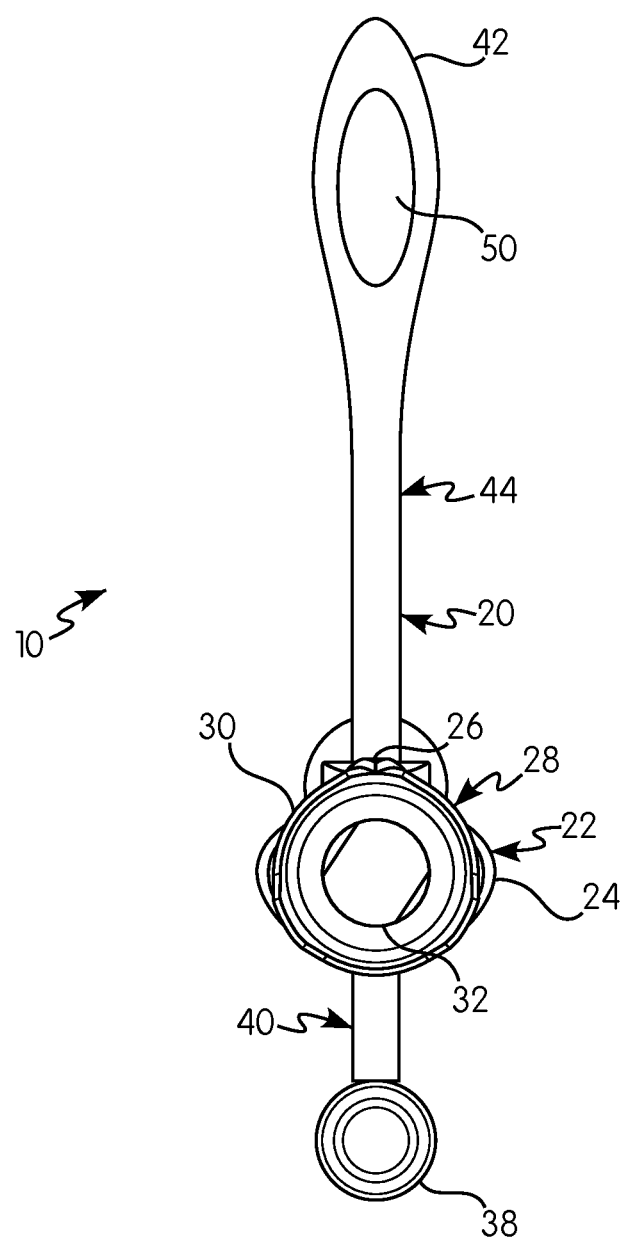
FIG. 3 is a bottom plan view of the acetabular cup extractor system of FIG. 1.
Figure 4:
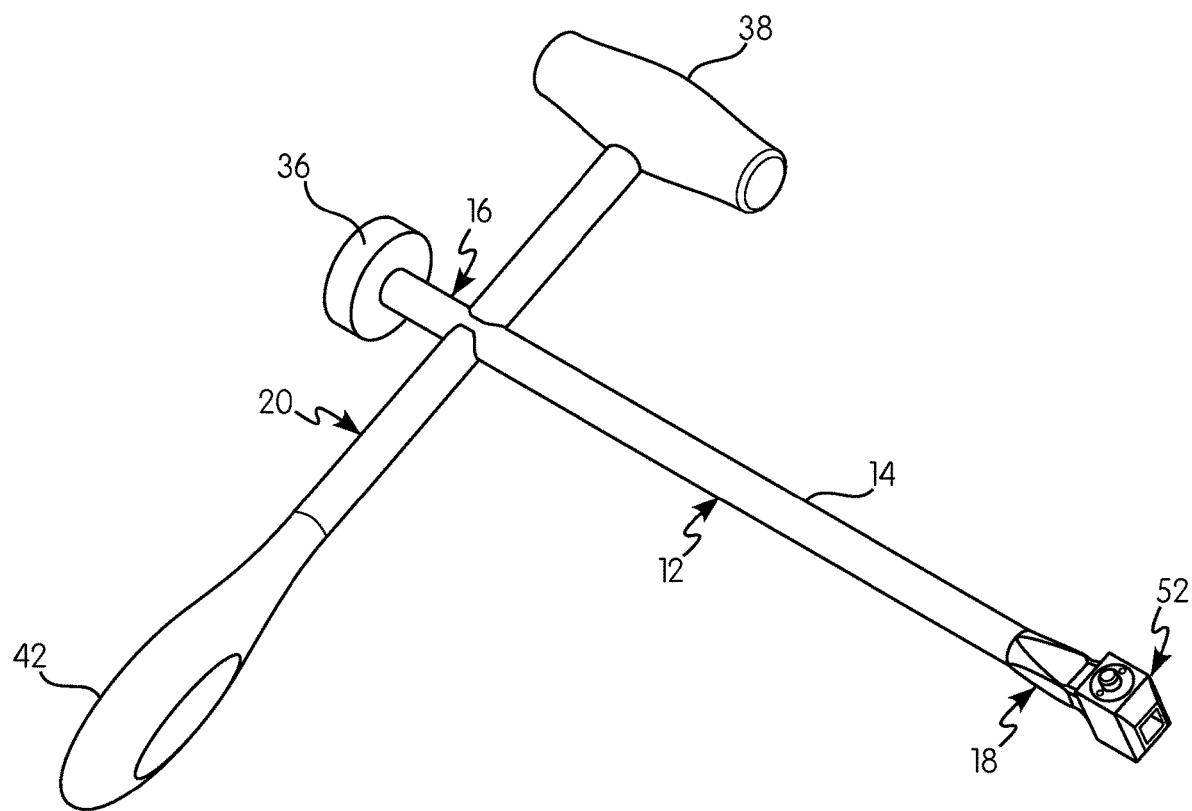
FIG. 4 is a bottom perspective view of a handle assembly of the acetabular cup extractor system of FIG. 1.
Figure 28:
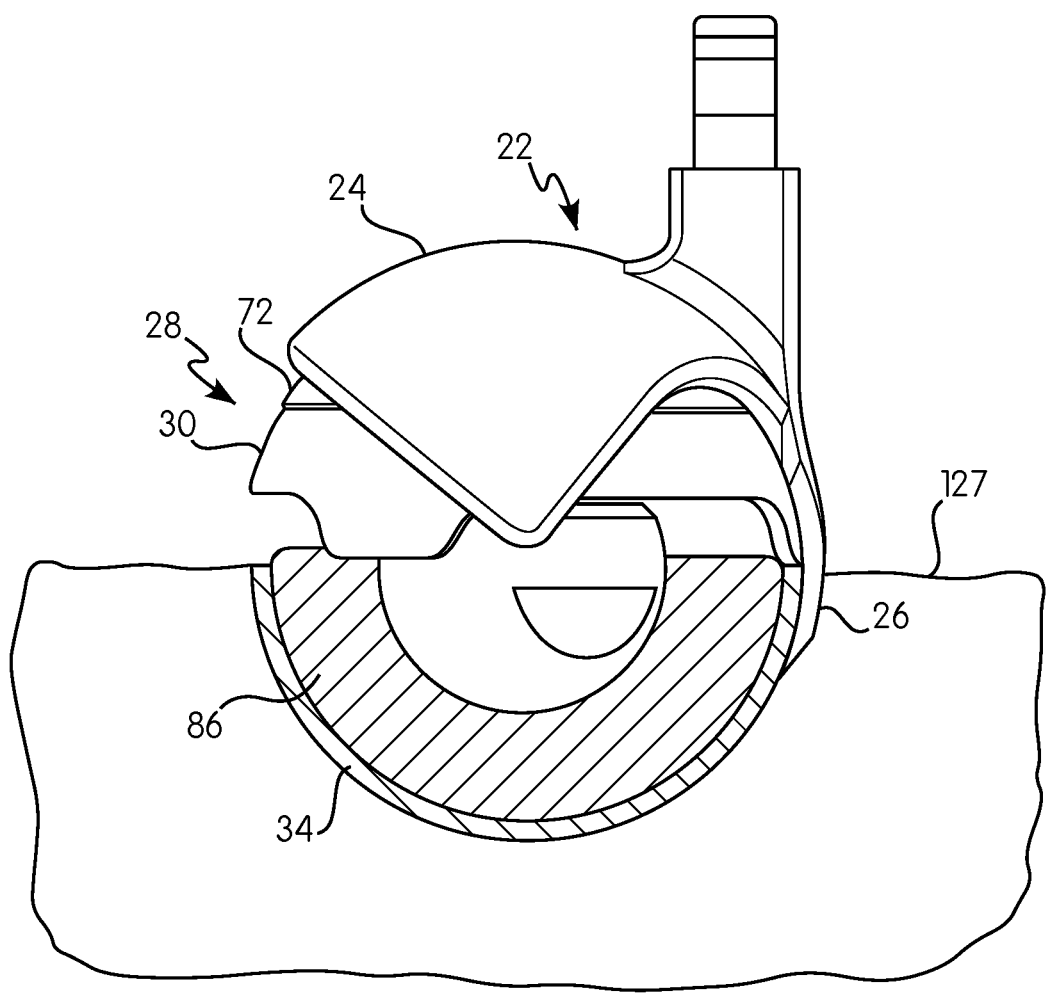
FIG. 28 is a right side view of the second extractor and the dome guide assembly of FIG. 12 shown piercing the acetabulum.

Referring now to the drawings, FIGS. 1-3 illustrate an exemplary embodiment of an acetabular cup extractor system 10 in accordance with the present disclosure. The acetabular cup extractor system 10 includes a handle 12, an extractor 22 and a dome guide assembly 28. The acetabular cup extractor is configured, e.g., as shown in FIGS. 1-3. The handle 12 includes an elongated shaft 14 having a proximal end 16, a distal end 18, and a transverse handle or lever assembly 20 extending substantially transverse to a longitudinal axis "A" of the elongated shaft. The extractor 22 is attachable to a distal end of the handle. The extractor includes a guide 24 and a blade 26. The dome guide assembly 28 includes a hemi-spherical dome 30 for engaging the extractor and a centering body 32 extending distally from the hemi-spherical dome for engaging an implant, such as acetabular implant 34 (FIG. 28).

The handle assembly or handle 12 of the acetabular cup extractor system 10 includes an elongated shaft having a distal end 18. The distal end engages a tool such as the extractor 22. The proximal end has an impact surface 36, as further discussed below. The handle 12 includes a lever assembly extending substantially transverse to the longitudinal axis "A" of the elongated shaft. The lever assembly includes a first gripping handle 38 extending away from a first lateral side of the elongated shaft 14, and a second gripping handle 42 extending away from a second lateral side of the elongated shaft 14 opposite the first lateral side.

The handle 12 is configured as shown in FIGS. 1-3. The proximal end 16 of the elongated shaft 14 includes an impact surface in the form of a proximally facing strike plate 36 adapted to be struck by a striking tool such as a hammer or the like. The strike plate includes an overall width larger than the overall width of the elongated shaft 14. While shown as being circular in shape, the striking plate 36 may assume other shapes including without limitation, square, oval, hexagonal, cone, triangle, frustum, cubical, and the like.

The transverse handle or lever assembly 20 is attached to the elongated shaft 14 about the proximal end 16 of the elongated shaft and includes the first gripping handle 38 extending away from the first lateral side of the elongated shaft 14 at a first end 40 of the transverse handle. The distal end or underside of the first gripping handle provides a striking surface 39 adapted for striking by a hammer or the like in order to extract the blade 26 from bone surrounding the acetabular implant. In addition, the proximal end or upper side of the first gripping handle provides an alternative striking face 41 that may be used in lieu of or in addition to striking plate 36.

In an exemplary embodiment of the first gripping handle 38 is configured as shown in FIGS. 1 and 3. The first gripping handle 38 is somewhat barrel-shaped and includes a longitudinal axis "B" that extends substantially transverse to a longitudinal axis "C" of the second gripping handle 42 and substantially parallel to the longitudinal axis "A" of the elongated shaft 14.

The transverse handle or lever assembly 20 further includes the second gripping handle 42 extending away from a second lateral side of the elongated shaft 14 opposite the first lateral side at a second end 44 of the transverse handle opposite the first end 40. The second gripping handle 42 is substantially club-shaped. The second gripping handle 42 includes a distally facing planar strike plate 50 adapted for striking by a hammer or the like in order to extract the blade 26 from bone surrounding the acetabular implant. A center 46 of the second gripping handle is spaced further from the longitudinal axis "A" of the elongated shaft 14 than a center 48 of the first gripping handle 38. Alternatively, the second gripping handle 42 may be spaced the same distance or less distance than the first gripping handle 38 from the longitudinal axis "A" of the elongated shaft 14.

The masses and locations of the first and second gripping handles 38, 42 are preferably such that substantial balance is achieved when the handle assembly is held in an upright position. In an exemplary embodiment, the handle assembly 12 has a mass of about 1 to 2 lbs., and preferably about 1.5 lbs., but can be more than 2 lbs. or less than 1 lb. A mass of the transverse handle or lever assembly 20 about the first lateral side of the elongated shaft 14 is substantially the same as a mass of the lever assembly about the second lateral side of the elongated shaft such that forces applied to the first gripping handle produces substantially similar torque force when a force is applied to the second gripping handle. In this way, torqueing of the handle is made easier when the blade 26 is inserted into bone surrounding an acetabular implant. In addition, the balance imparted by the handle 12 assures firm and reliable contact between the mating surfaces of the extractors 22, 122 and the guide assembly 28.

The elongated shaft 14 has a length of about 6 to about 30 inches, preferably about 8 to about 24 inches, and more preferably about 10 to about 18 inches, but can be more or less than the foregoing ranges. In an exemplary embodiment, the elongated shaft 14 has an overall length greater than an overall longitudinal length of the transverse handle or lever assembly 20. In another exemplary embodiment, the elongated shaft 14 has an overall length substantially the same as an overall longitudinal length of the transverse handle or lever assembly 20. The elongated shaft also includes a fastener 52, discussed below.

Figure 5:
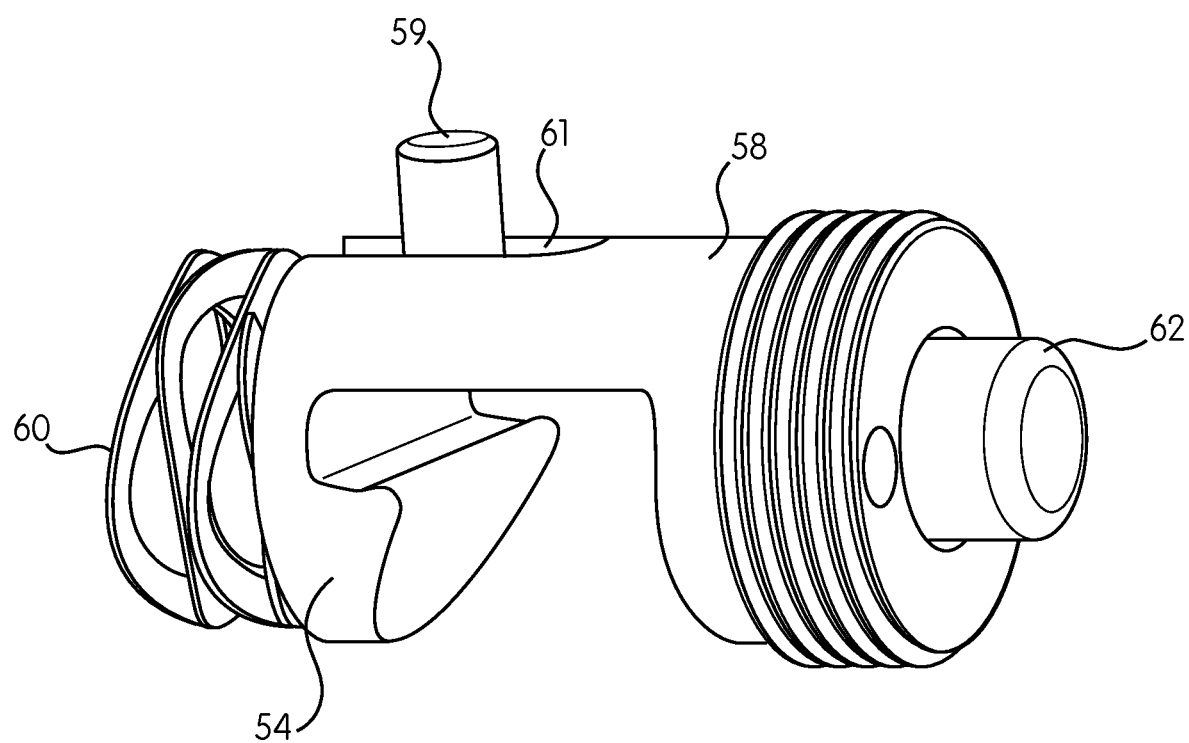
FIG. 5 is a perspective view of a detent assembly of the acetabular cup extractor system of FIG. 1.
Figure 6:
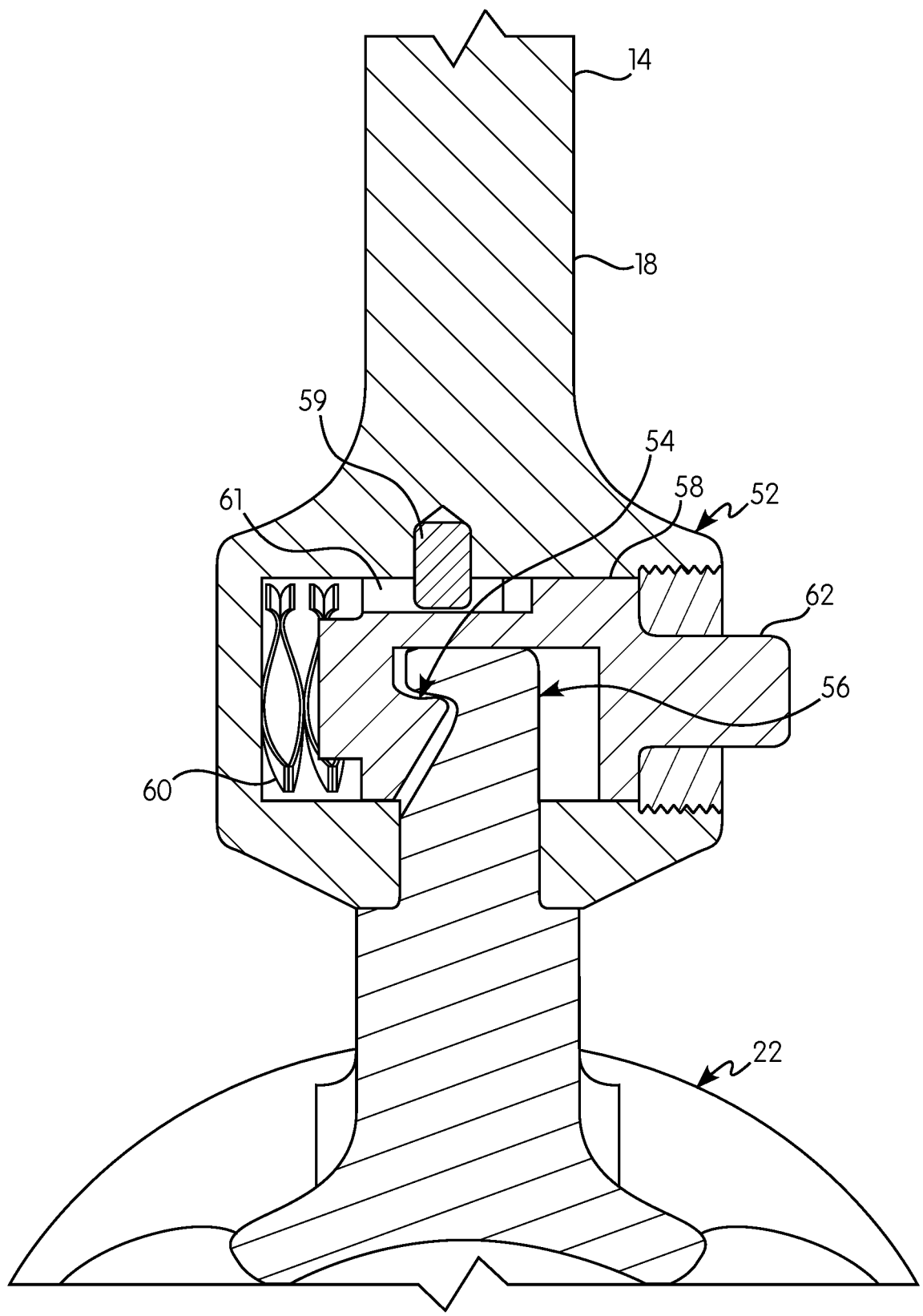
FIG. 6 is a partial cross-sectional view of the detent assembly of FIG. 5 joining the handle assembly with an extractor of the acetabular cup extractor system of FIG. 1.

Referring to FIGS. 1, 2, 4 and 5, the fastener 52 is positioned about the distal end 18 of the elongated shaft for connecting to the tool or extractor 22 and in an exemplary embodiment, includes a detent 54 for engaging a cooperating detent 56 of the tool 22. As illustrated in FIGS. 5 and 6, the fastener 52 comprises the detent 54 which is configured to include a ramped surface (and is part of a sliding latch member 58), and the extractor 22 is provided with a cooperating detent 56 which is configured for engagement with the detent 54. The fastener 52 further includes a biasing member 60 for biasing the detent 54 into engagement with the cooperating detent 56 of the extractor 22. The biasing member can be any suitable biasing member, e.g., a coil spring, a leaf spring, an elastomer, and the like.

A release mechanism 62 enables a user to overcome the biasing force of the biasing member 60 and release the detents 54, 56 from one another when it is desired to remove the extractor 22 from the fastener 52. In an exemplary embodiment, the fastener 52 includes a centering member 59 for engaging a slot 61 provided in the sliding latch member 58 to maintain the orientation and securing of the sliding latch member 58 during engagement and disengagement of the detents 54, 56.

Figure 7:
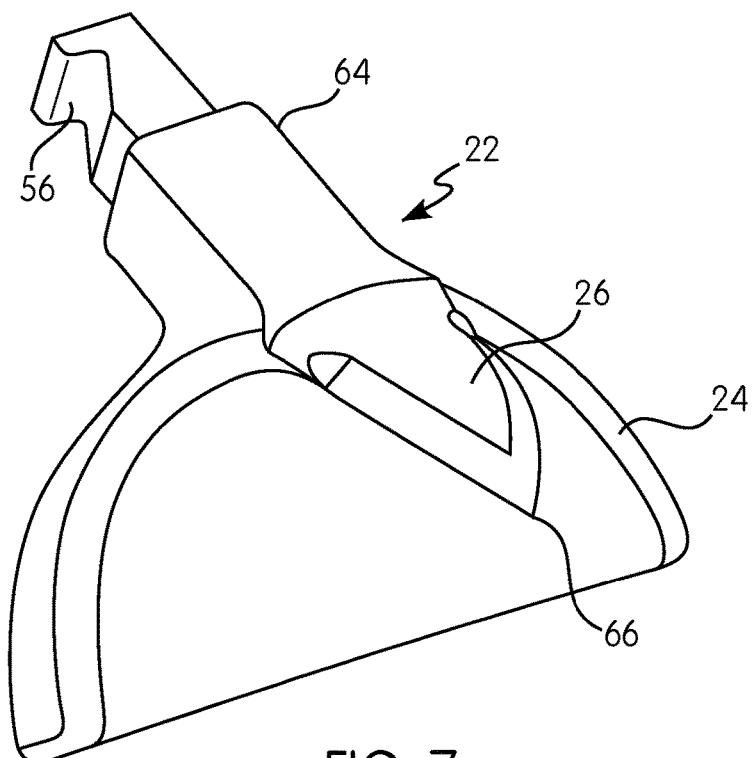
FIG. 7 is a bottom perspective view of an extractor of the acetabular cup extractor system of FIG. 1.
Figure 8:
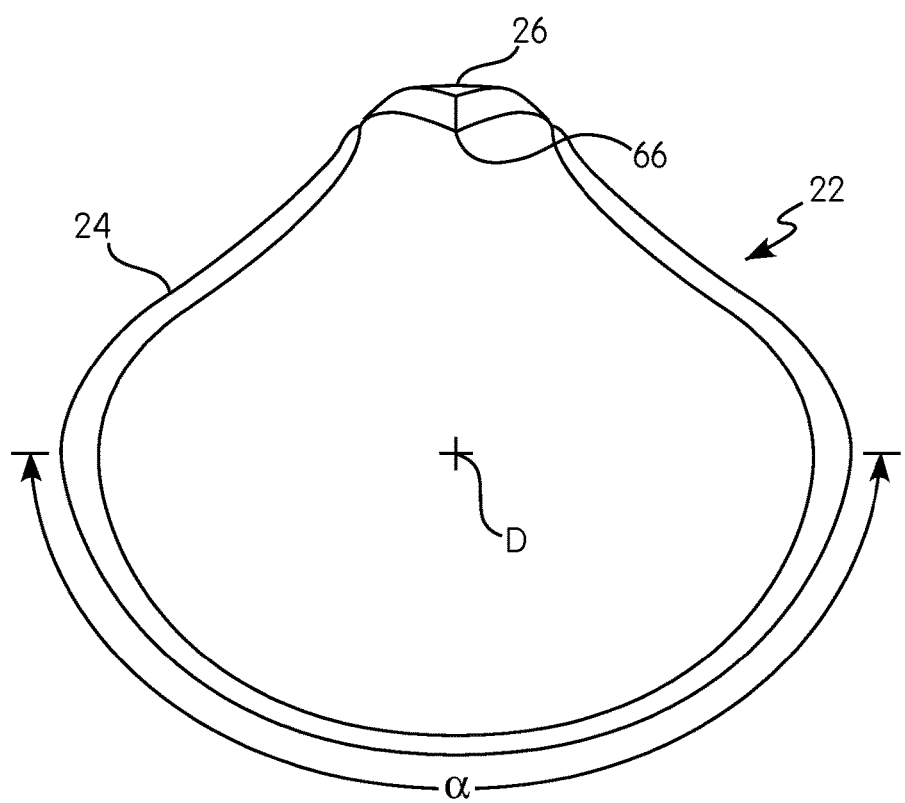
FIG. 8 is a bottom plan view of the extractor of FIG. 7.
Figures 9, 11:
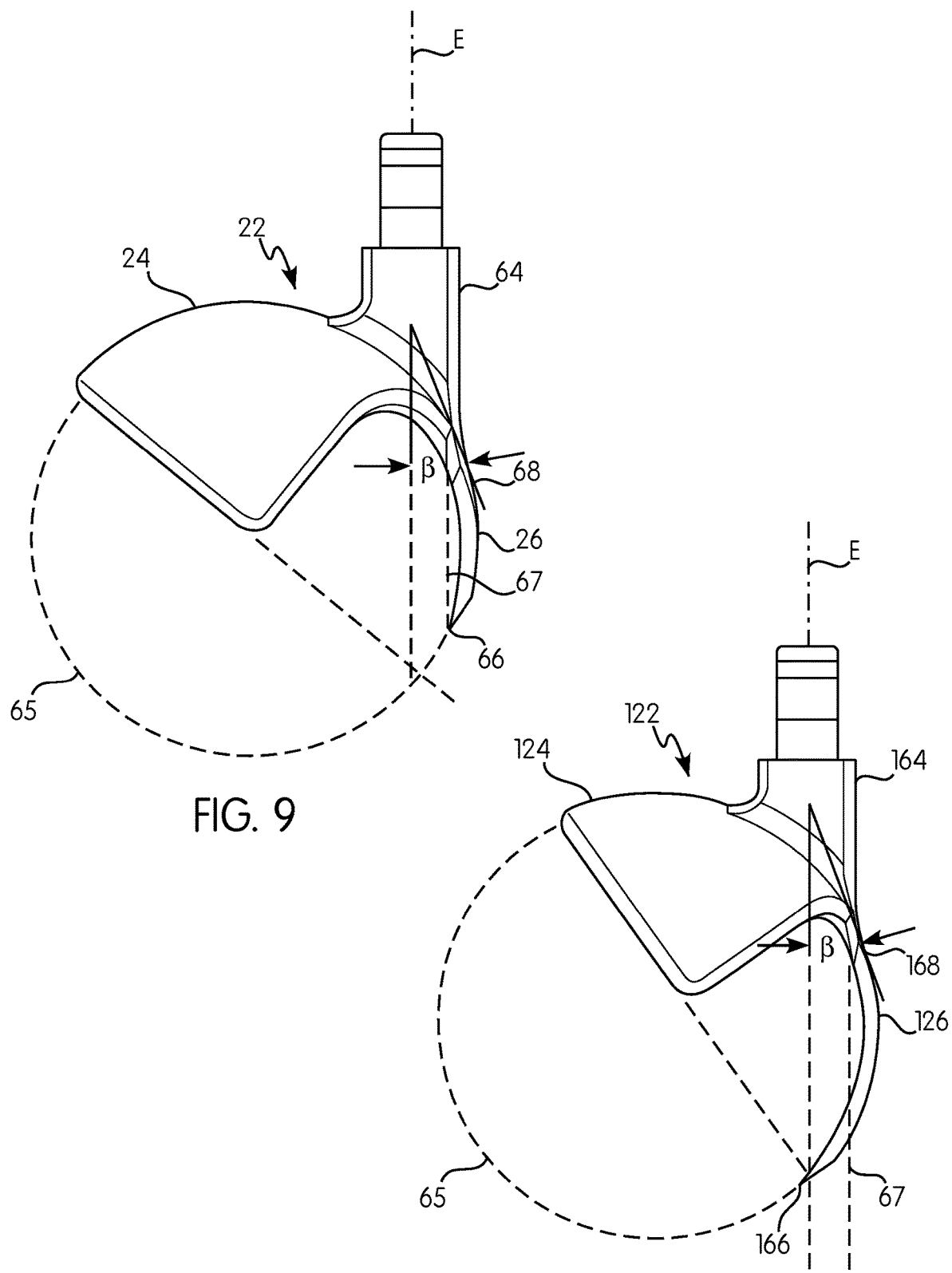
FIG. 9 is a side elevational view of the extractor of FIG. 7.
FIG. 11 is a right side elevational view of the second extractor of the acetabular cup extractor system of FIG. 10.

Referring to FIGS. 7-9, there is shown the tool or extractor 22 in accordance with an exemplary embodiment of the subject disclosure. The extractor includes the hub or mount 64 for engaging the handle, the hemi-spherical shell-like guide 24 extending from the hub, and the blade 26 extending from one of the hub 64 and the hemi-spherical shell-like guide 24. By being hemi-spherical like in shape, the hemi-spherical shell-like guide 24 is curved or concave in shape and adapted to substantially matingly engage a hemi-spherical dome assembly 30 of the dome guide assembly 28 (see FIG. 1). The hub 64 is configured to engage the handle 12. More particularly, the hub 64 includes the cooperating detent 56 for engaging the detent 54 of the fastener 52 of the elongated shaft 14.

In an exemplary embodiment, as shown in FIG. 8, the hemi-spherical shell-like guide 24 extends a revolution or arc "α" of about 180 degrees relative to a central axis "D" of the hemi-spherical shell-like guide. Alternatively, the hemi-spherical shell-like guide can extend more or less than 180 degrees, e.g., 90, 95, 100, 110, 120, 130, 140, 150, 160, 170, 190, 200, 210, 220 and 230 degrees. In any event, the walls of the hemi-spherical shell-like guide extend from the top of the hemi-spherical shell-like guide to cover a substantial portion of the hemi-spherical dome assembly 30 of the dome guide assembly 28. The same is true of hemi-spherical shell-like guide 124 shown in FIG. 11.

As shown in FIG. 9, the hub 64 extends from the hemi-spherical shell-like guide 24 such that a longitudinal axis "E" of the hub extends through a circle 65 defined by an arc of an outer surface of the hemi-spherical shell-like guide in a chord-like fashion.

The blade 26 of the extractor 22 is an arcuate or curved blade so as to closely accommodate the outer shape of an acetabular cup implant to be extracted. The hemi-spherical shell-like guide 24 extends from the hub or mount 64 and the blade 26 extends from the hub or mount in a direction opposite the guide. Blade 26 is curved in both its longitudinal direction and in a widthwise extent transverse to the longitudinal direction. Blade 26 includes a point 66 directed substantially distally from the hub 64. Blade 26 also extends along a path defined by an arc path of the hemi-spherical shell-like guide and is also positioned centrally between opposing ends of the hemi-spherical shell-like guide (FIG. 8).

In addition, as shown in FIG. 9, blade 26 is constructed such that a tangency of a surface of a base 68 of the blade is at a non-zero angle "β" relative to a longitudinal axis "E" of the hub. Likewise, a similar tangency 168 exists for blade 126 as illustrated in FIG. 11. The angle β can be e.g., 20, 25, 30, 40, 50, 60, 70 degrees.

According to an embodiment as best shown in FIG. 9, blade 26 extends distally from the hub 64 an arc length of about 45-80 degrees. The blade 26 may also extend from the hub an arc length of more or less than 45-80 degrees, e.g., 35, 40, 45, 50, 55, 60, 65, 70, 75, 80, 85, 90 degrees. In addition, the hemi-spherical shell-like guide 24 extends distally from the hub 64 an arc of about 80-90 degrees, but may alternatively extend an arc length of about 60, 70, 75, 85, 95, 100 degrees.

Furthermore, as shown in FIG. 9, a portion of the blade 26 extends beyond a plane 67 defined by a side of the hub. Also when the extractor 22 is attached to the handle, the blade can extend beyond a plane defined by a side of the elongated shaft of the handle.

Figure 10:
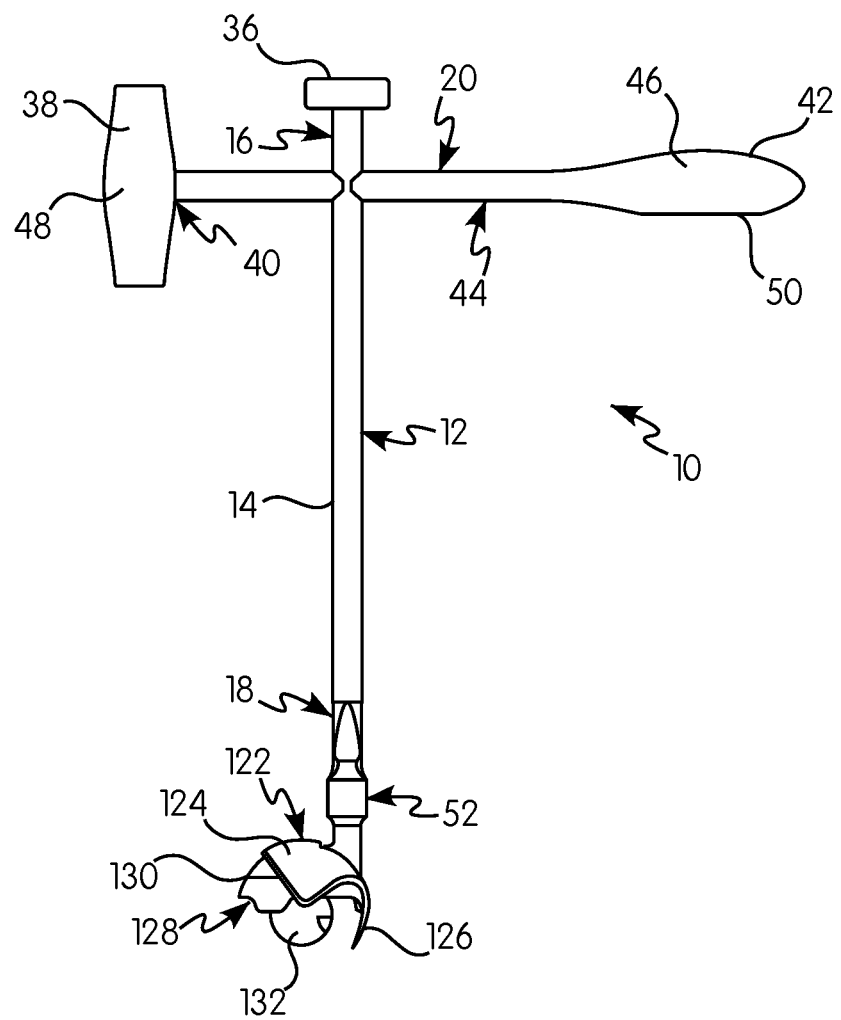
FIG. 10 is a right side elevational view of an orthopedic instrument in the form of an acetabular cup extractor system to which is mounted a second extractor in accordance with the subject disclosure.

FIG. 10 illustrates another extractor 122 attached to the handle 10. The structure and function of the "second" tool or extractor 122 is shown in FIG. 11 and is similar to blade 26 except as described below. The blade 126 is arcuate or curved blade so as to closely accommodate the outer shape of an acetabular cup implant to be extracted. The hemi-spherical shell-like guide 124 extends from the hub or mount 164 and the blade 126 extends from the hub or mount in a direction opposite the hemi-spherical shell-like guide. The blade 126 is curved in both its longitudinal direction and in a widthwise extent transverse to the longitudinal direction. Blade 126 includes a point 166 directed substantially distally from the hub 164. Blade 126 also extends along a path defined by an arc path of the hemi-spherical shell-like guide and is also positioned centrally between opposing ends of the hemi-spherical shell-like guide.

As best shown in FIG. 11, the blade 126 of the second extractor 122 extends distally from the hub 164 an arc length of at least about 80-120 degrees, e.g., 80, 85, 90, 95, 100, 105, 110, 115, 120 degrees. In addition, the hemi-spherical shell-like guide 124 extends distally from the hub 164 an arc of about 45-80 degrees. That is, the hemi-spherical shell-like guide 124 may extend from the hub more or less than 45-80 degrees, e.g., 35, 40, 45, 50, 55, 60, 65, 70, 75, 80, 85, 90 degrees. In an embodiment, the point 166 of the blade 126 extends to about a most distal point of the hemi-spherical shell-like guide 124. The point 166 of the blade 126 can alternatively extend beyond a most distal point of the hemi-spherical shell-like guide 124. The blade 126 is a finishing blade having an overall length greater than the blade 26 of the extractor 22, which is also known as a starter blade.

Furthermore, as shown in FIG. 11, a portion of the blade 126 extends beyond a plane 167 defined by a side of the hub. Also when the extractor 122 is attached to the handle, the blade 126 can extend beyond a plane defined by a side of the elongated shaft of the handle Referring to FIGS. 12-17, there is shown an exemplary embodiment of the dome guide assembly 28. The dome guide assembly 28 includes a dome shape on an upper end thereof in the form of a dome comprising a hemi-spherical dome assembly 30. The dome guide assembly 28 further comprises a sphere-like or spherical-like centering body (or, simply, body) 32 (FIG. 10) extending distally from the hemi-spherical dome assembly which is sized and shaped to engage an acetabular implant or be received within an acetabular implant similar to the manner shown in FIG. 28.

Figure 12:
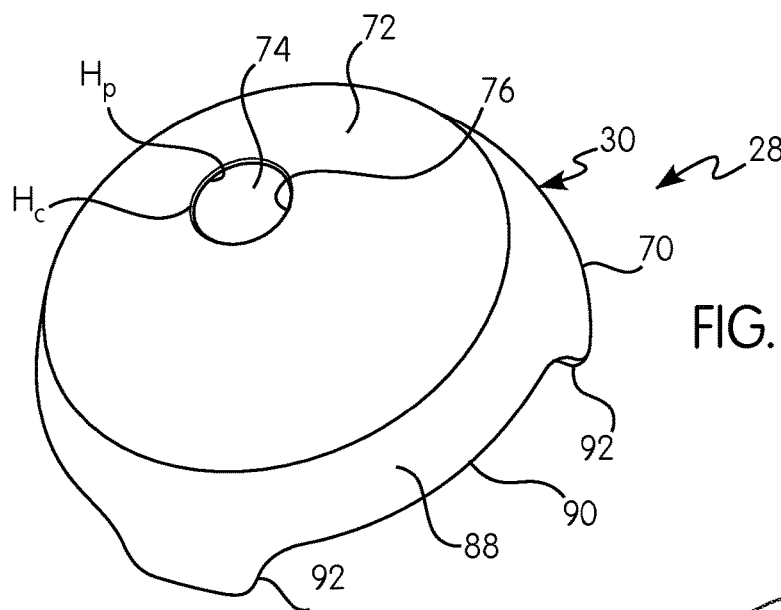
FIG. 12 is a top perspective view of a dome guide assembly of the acetabular cup extractor system of the subject disclosure.
Figure 13:
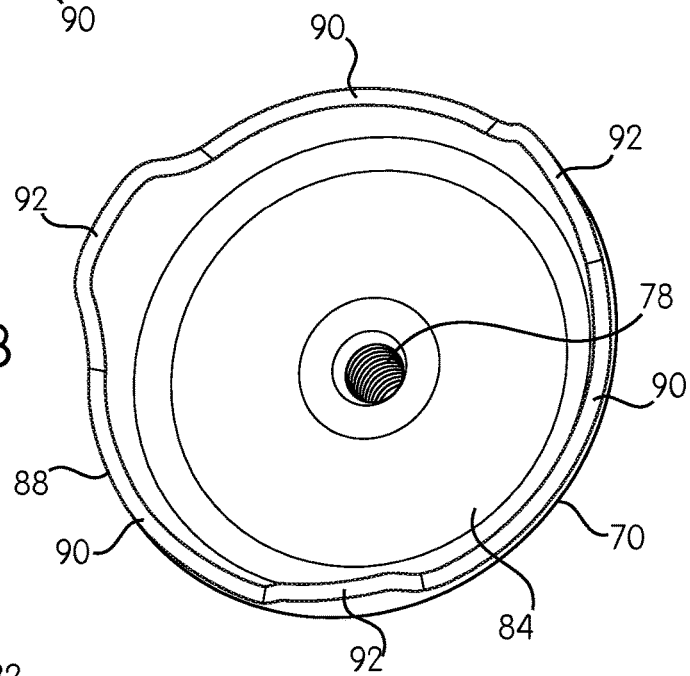
FIG. 13 is a bottom perspective view of a centering body of the dome guide assembly of FIG. 12.
Figure 14:
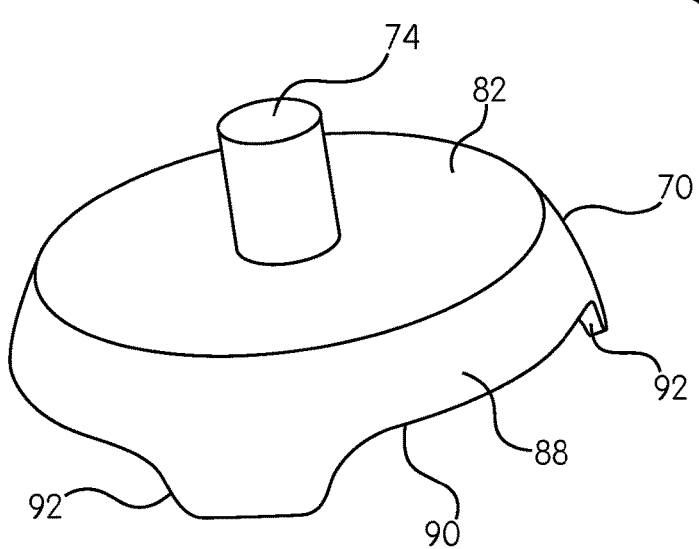
FIG. 14 is a top perspective view of the centering body of FIG. 13.
Figure 15:
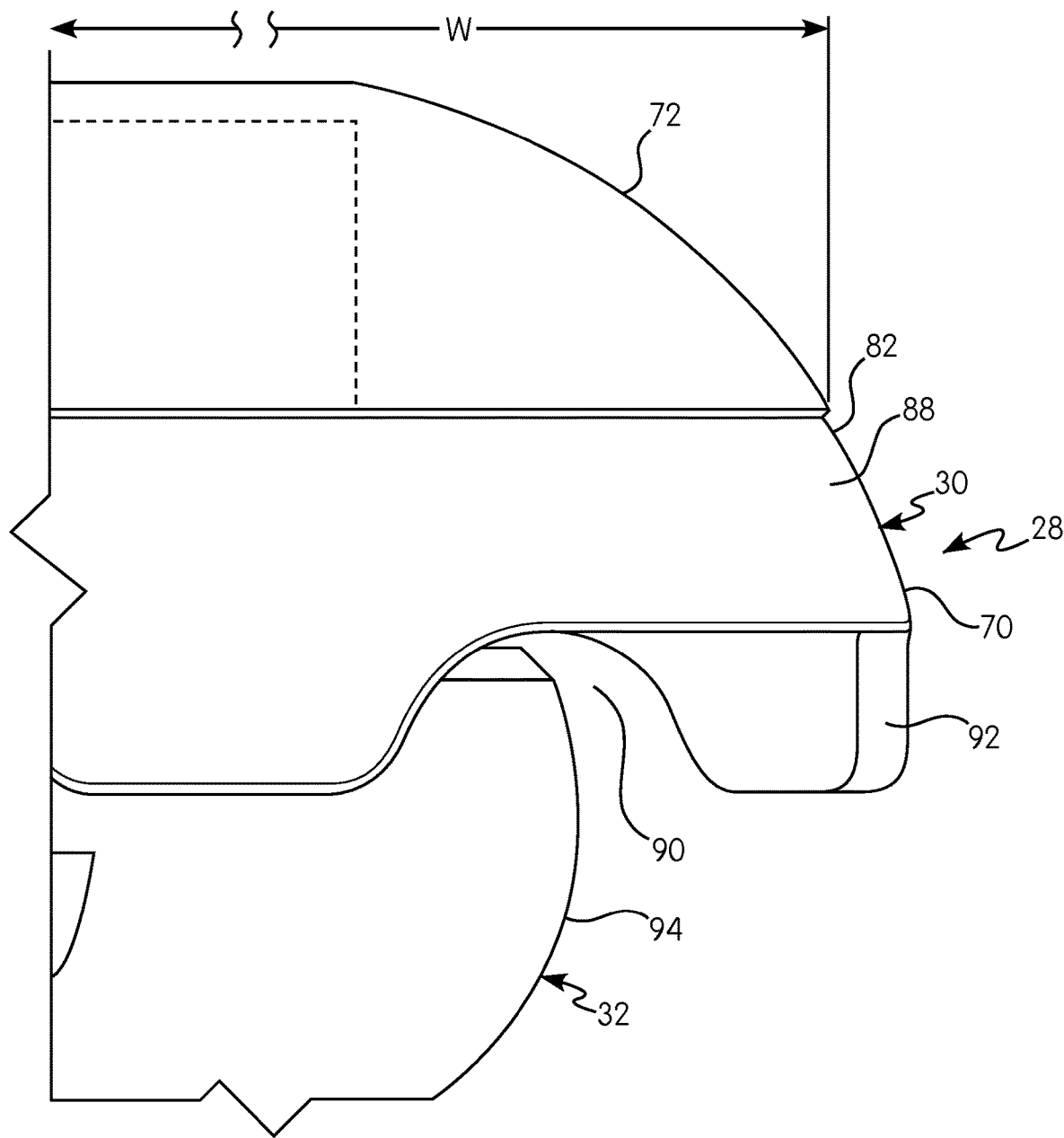
FIG. 15 is an enlarged partial side elevational view of the dome guide assembly of FIG. 12.

As shown in FIGS. 12-15, the hemi-spherical dome assembly 30 includes a mount 70 and a dome-like cap 72 mounted to the mount 70. The mount includes a post 74 and the dome-like cap 72 includes a through hole 76 for receiving the mount, in particular, the post 74. As shown in FIG. 13, the post includes a fastener 78, e.g., threading or the like for connecting with a cooperating fastener 80 (FIGS. 16 and 17) such as threading or the like provided on the centering body 32. As shown in FIG. 15, the dome-like cap 72 has an overall width "W" greater than an upper surface 82 of the mount 70. As shown in FIG. 12, the dome-like cap has an overall height "Hc" greater than an overall height "Hp" of the post 74. The dome-like cap can be formed out of a polymer, e.g., ultra high molecular weight polyethylene, and the like, or a composite, e.g., ceramic or a metal with a low-friction coating.

Referring to FIG. 13, the mount 70 includes an undercut relief 84. As shown in FIGS. 12-15, the mount includes a skirt 88 having a spherical shell-like curvature. The skirt includes a plurality of spaced apart cutouts 90 and/or a plurality of spaced apart legs 92. The legs are sized and configured to rest atop a perimeter of an acetabular implant.

Figure 16:
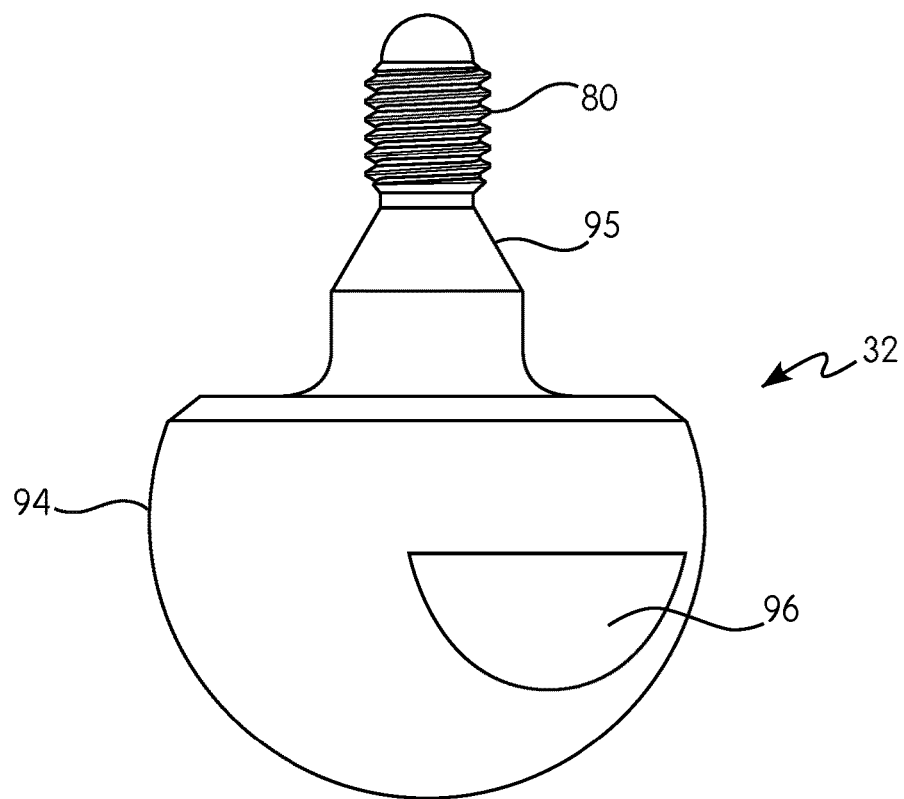
FIG. 16 is an elevational view of a centering body of the dome guide assembly of FIG. 12.
Figure 17:
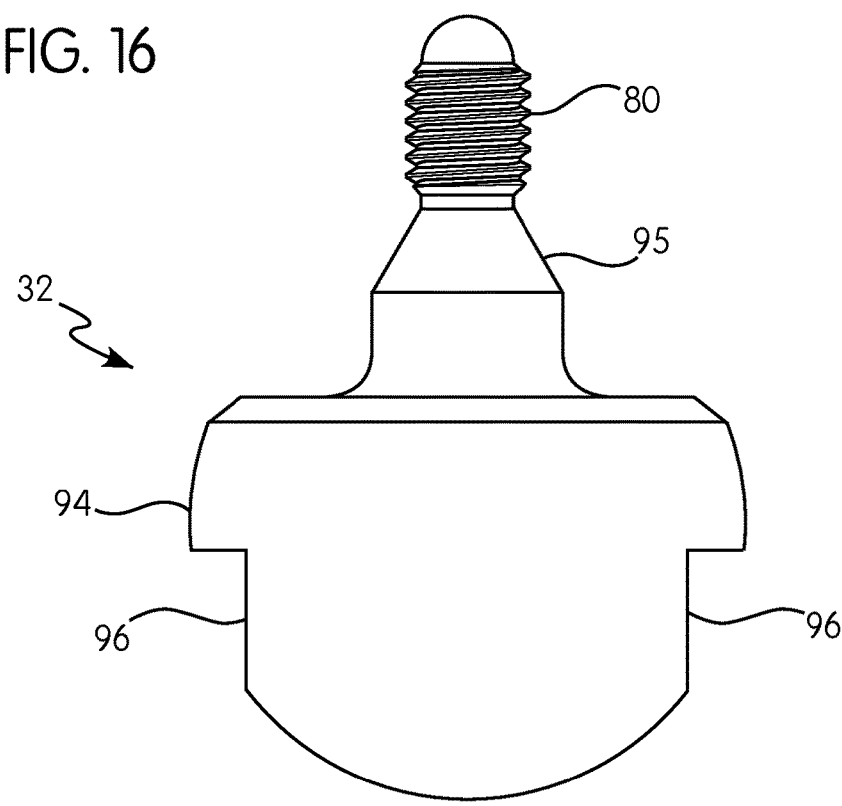
FIG. 17 is another elevational view of the centering body of FIG. 16.

As shown in FIGS. 15-17, the spherical-like centering body 32 includes a sphere-like body 94 and a mounting member 95 extending from the spherical-like body for connecting with the hemi-spherical dome assembly 30. The mounting member includes threading 80, although it may alternatively include other types of fasteners for releasably connecting the spherical-like centering body 32 to the hemi-spherical dome assembly 30. In the case that the mounting member is formed as threading 80 and the post includes a correspondingly threaded fastener such as female threading 78, the spherical-like centering body 32 can be provided with a pair of opposed flats 96 (FIG. 17) on its lateral sides which are adapted to be engaged by a turning tool such as a wrench or the like in order to securely connect the spherical-like centering body 32 to the hemi-spherical dome assembly 30. Such a threaded connection also makes it easy and convenient to replace the spherical-like centering body 32 with spherical-like centering bodies of different sizes to fit in acetabular cup implant liners of different sizes for optimum fit between the selected spherical-like centering body and the acetabular cup implant liner.

In an exemplary embodiment, the acetabular extraction system may be arranged as a kit containing spherical-like centering bodies of different sizes, hemi-spherical dome assemblies of different sizes, and extractors of different sizes to accommodate differently sized acetabular implants and liners therefor. For example, the kit may include a plurality of extractors, spherical-like centering bodies and hemi-spherical dome assemblies of different sizes, e.g., overall widths that match different sizes of various acetabular implant and implant liner sizes.

Figure 18:
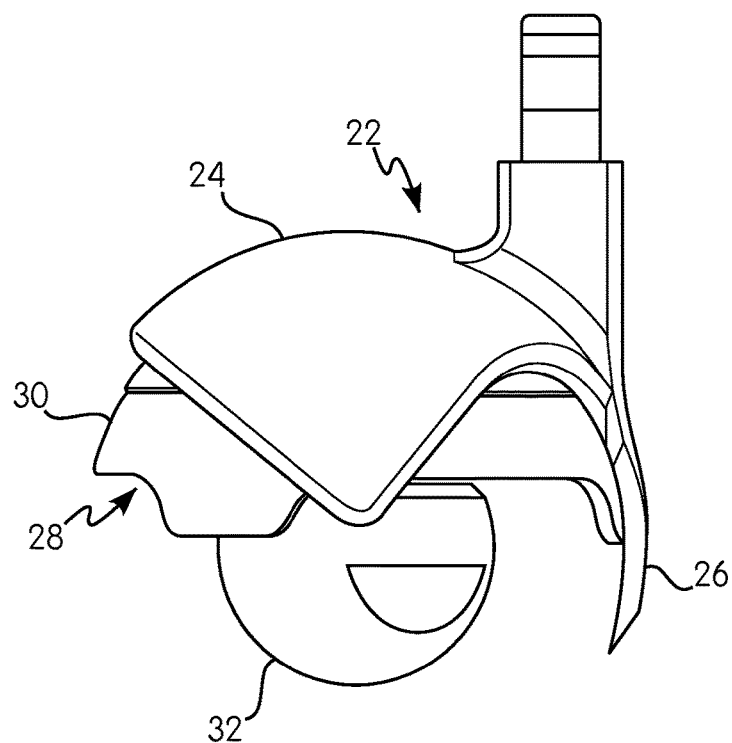
FIG. 18 is a right side elevational view of the extractor and the dome guide assembly of the acetabular cup extractor system of FIG. 12.
Figure 19:
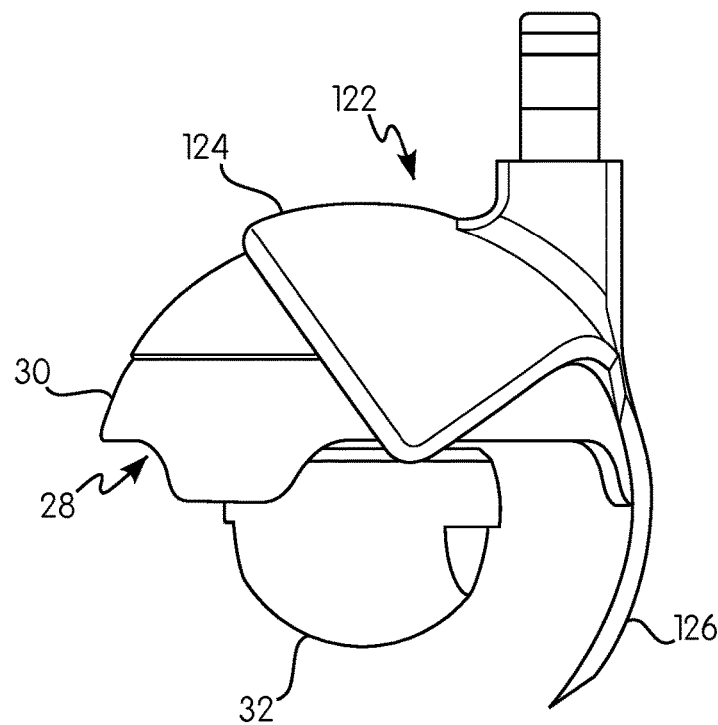
FIG. 19 is a right side elevational view of the second extractor and the dome guide assembly of FIG. 12.

FIG. 18 illustrates a view of the engagement between the extractor 22 and the dome guide assembly 28. FIG. 19 illustrates a view of the engagement between the second extractor 122 and the guide assembly 28. These figures depict the position the blades would be in when inserted into bone.

Figure 20:
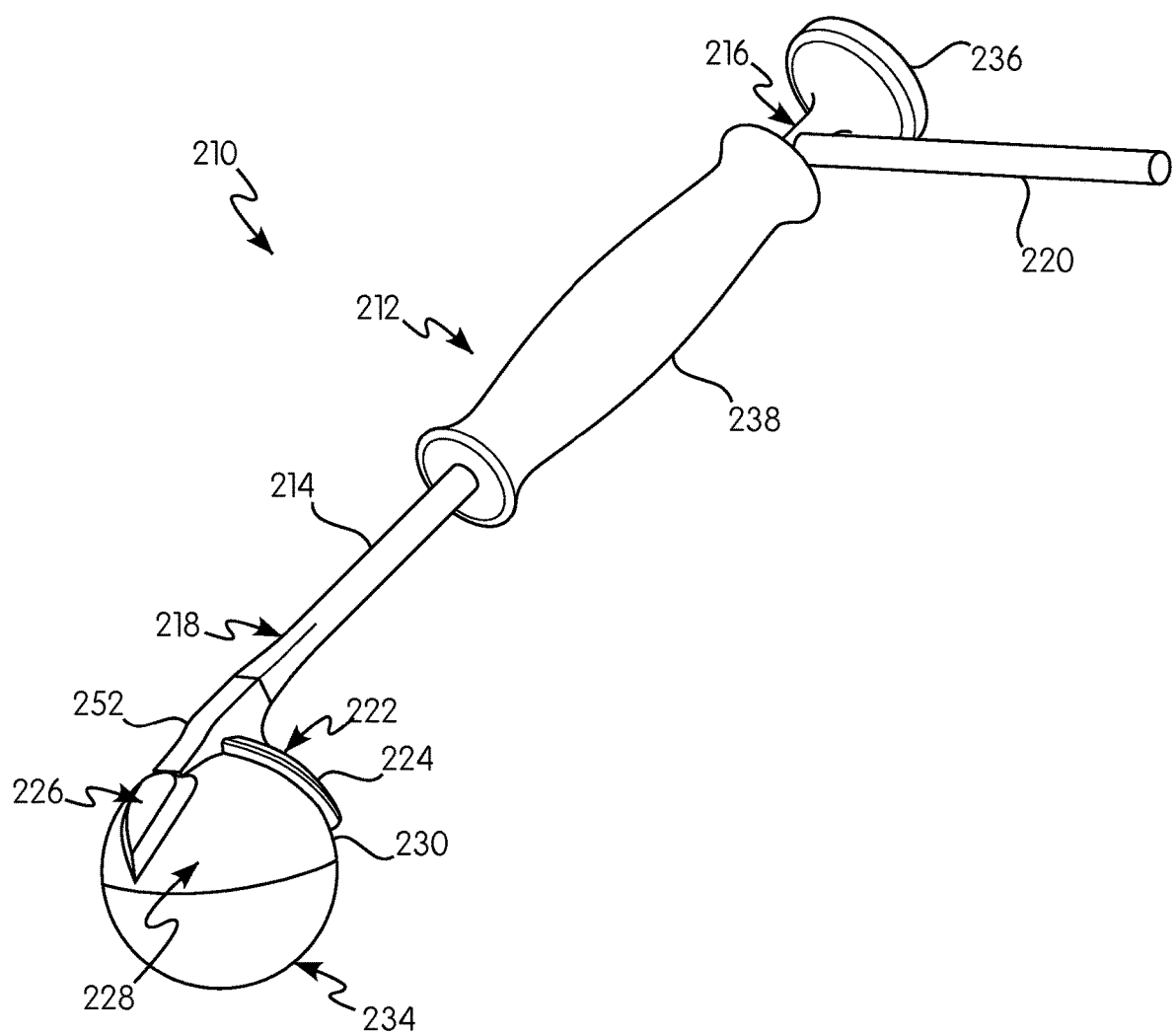
FIG. 20 is a perspective view of an acetabular cup extractor system in accordance with another exemplary embodiment of the subject disclosure shown in contact with an acetabular cup implant.
Figure 21:
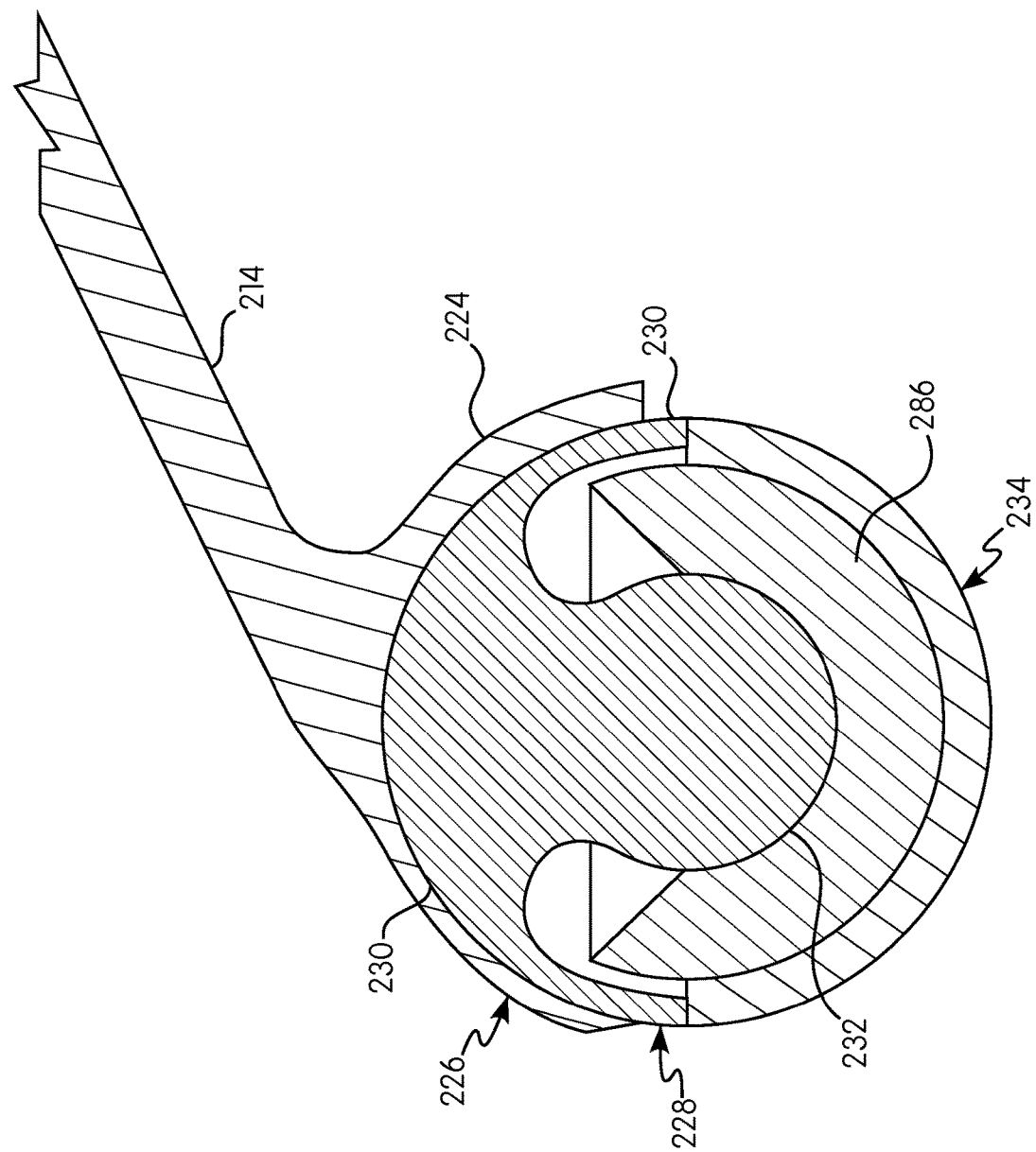
FIG. 21 is enlarged cross-sectional view of a lower portion of the acetabular cup extractor system of FIG. 20 shown in contact with an acetabular cup implant.
Figure 22:
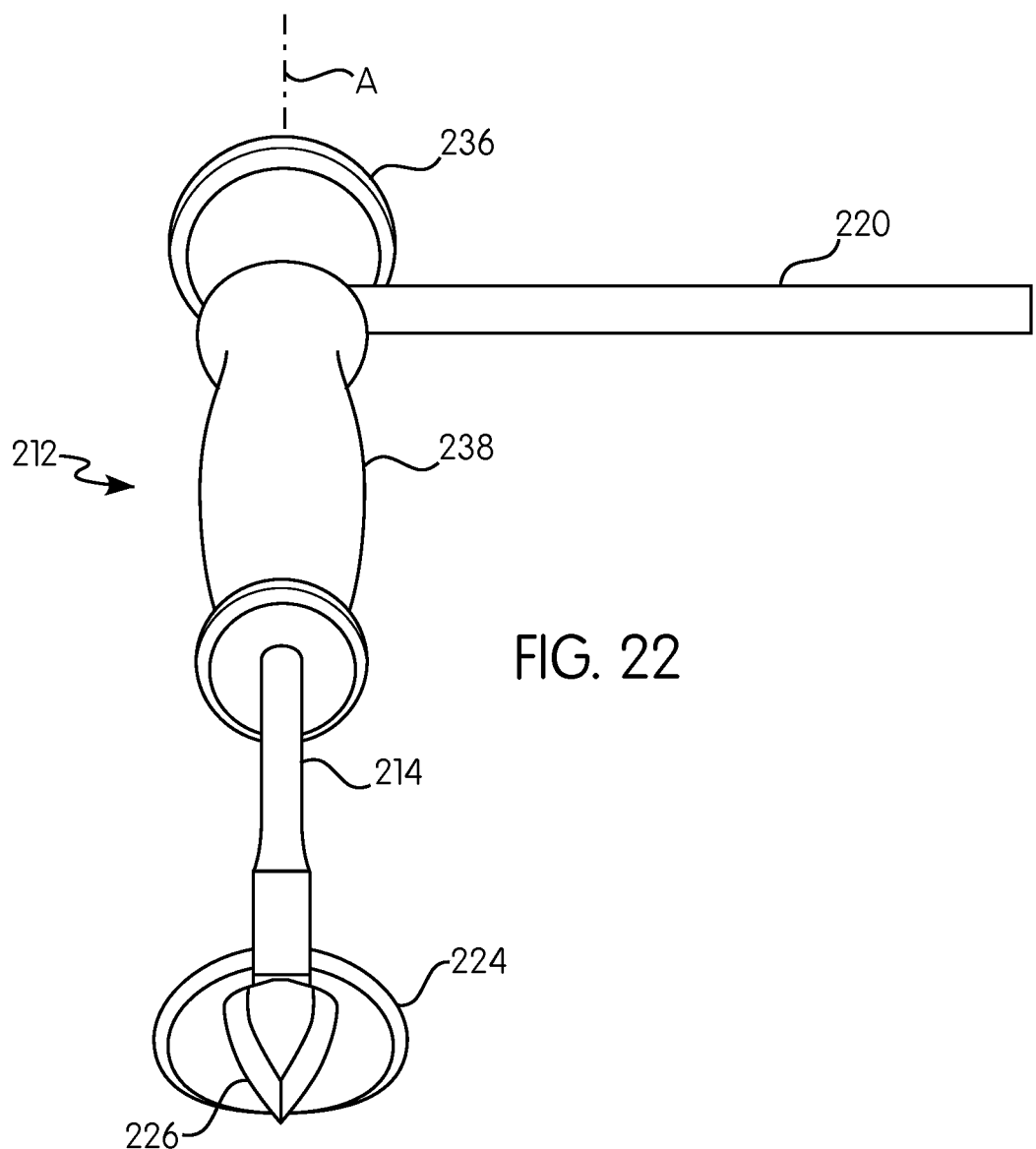
FIG. 22 is a perspective view of the acetabular cup extractor system of FIG. 20.

Referring to FIGS. 20-22, there is illustrated a second exemplary embodiment of an acetabular cup extraction system 210 in accordance with the subject disclosure. The acetabular cup extraction system 210 comprises a handle assembly 212, a tool in the form of an extractor 222, and a dome guide assembly 228. The handle assembly includes an elongated shaft 214 having a proximal end 216, a distal end 218 for engaging a tool, and a transverse handle or lever assembly 220 extending substantially transverse to a longitudinal axis "A" (FIG. 22) of the elongated shaft. The extractor 222 extends from the distal end of the handle. The extractor includes a guide 224 and a blade 226. The dome guide assembly 228 includes a hemi-spherical dome 230 for engaging the extractor and a centering body 232 (FIG. 21) extending distally from the hemi-spherical dome for engaging a liner 286 of an implant, such as acetabular implant 234.

About the proximal end 216 of the elongated shaft 214 is an impact surface in the form of a proximally facing strike plate 236 adapted to be struck by a striking tool such as a hammer or the like. In order to assure reliable striking by the striking tool, the strike plate includes an overall width larger than the overall width of the elongated shaft 214.

The transverse handle or lever assembly 220 is attached to the elongated shaft 214 adjacent the proximal end 216 of the elongated shaft. The transverse handle 220 may be engaged by a user's hand and functions substantially similarly to the second gripping handle 42 described above. The elongated shaft 214 includes a first gripping handle 238 extending coaxially therewith with the transverse handle or lever assembly 220 functioning as a second gripping handle.

In an embodiment, the guide 224 is configured as a hemi-spherical shell-like guide. The hemi-spherical shell-like guide 224 is curved and concave in shape and adapted to substantially matingly engage the dome assembly 228 of a dome guide assembly 328 (FIG. 21)

Figure 23:
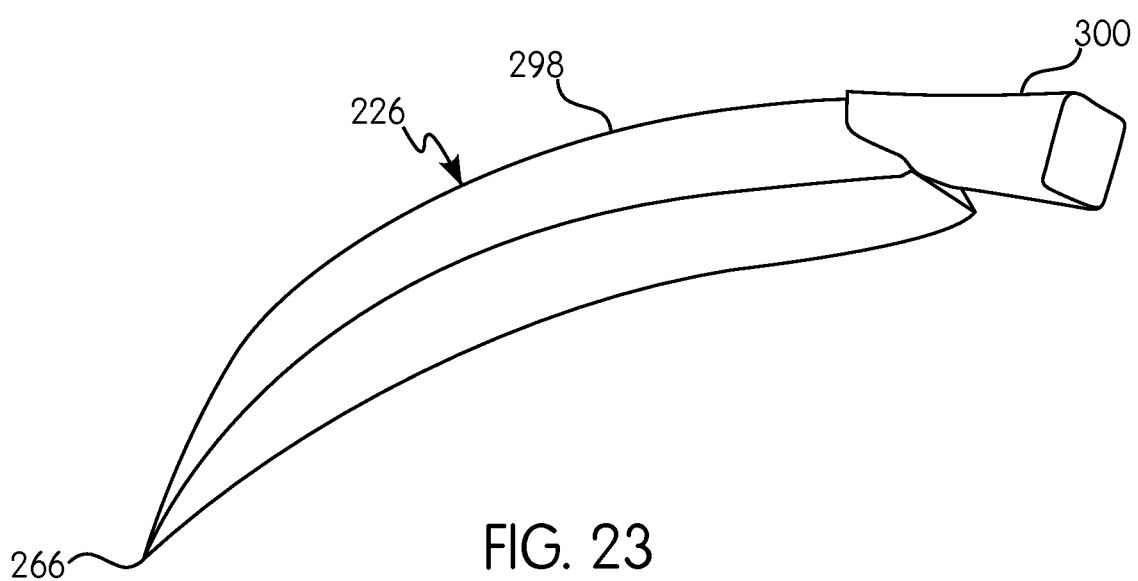
FIG. 23 is a perspective view of a cutting blade of an extractor of the acetabular cup extractor system of FIG. 20.

Referring to FIG. 23, there is shown in enlarged view the construction of the blade 226. In an exemplary embodiment, the blade 226 includes blade portion 298 and a connector portion 300 adapted for detachable connection to a fastener 252 (FIG. 20) located at the distal end 218 of the elongated shaft 214. The blade 226, like blade 26 and blade 126 discussed above, is arcuate or curved so as to closely accommodate the outer shape of an acetabular cup implant to be extracted such as cup implant 34 (FIGS. 20 and 21). In an exemplary embodiment, the blade 226 is curved in both its longitudinal direction and in a widthwise extent transverse to the longitudinal direction and has a point 266 at its distal end.

The fastener 252 can be constructed, e.g., as a clasp-like fastener for releasably receiving connector portion 300 of the blade 226 so that a differently-shaped and/or sized blade may be selectively attached to the acetabular cup extraction system 210 in order to effectuate deeper bone cuts similar to blade 126 of extractor 122 discussed above. Alternately, the fastener may assume other forms of fastener configurations including, but not limited to threading, detents, clamping or friction-fit.

Figure 24:
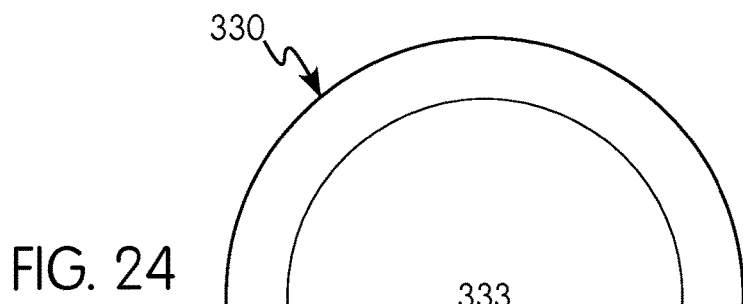
FIG. 24 is a top plan view of a dome guide assembly for use in the acetabular cup extractor system of FIG. 20.
Figure 25:
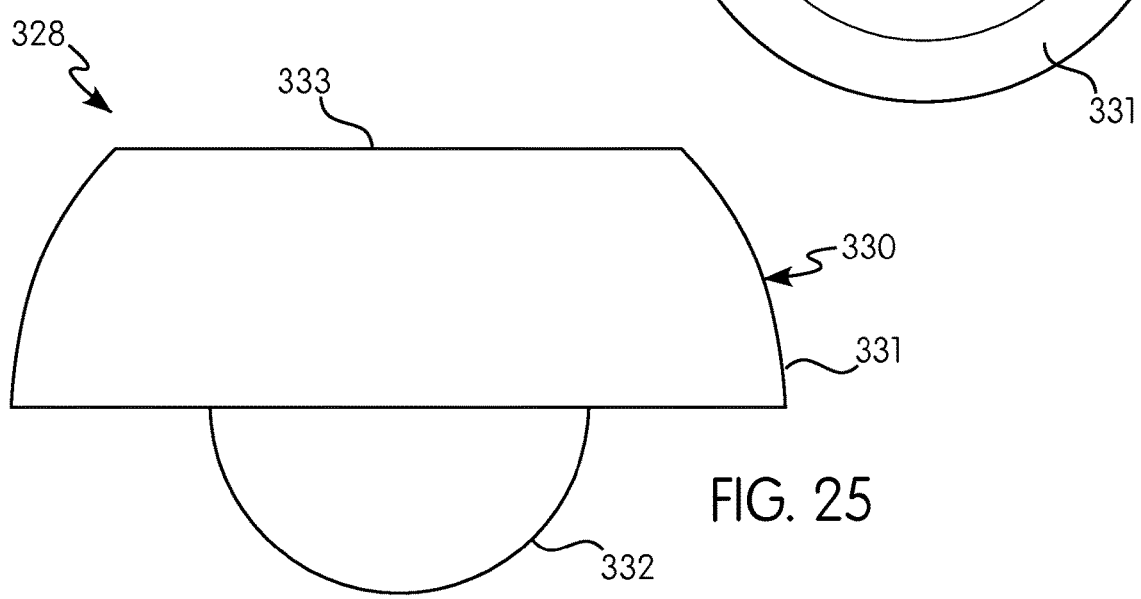
FIG. 25 is a side elevational view of the dome guide assembly of FIG. 24.

Referring to FIGS. 24 and 25, there is illustrated another exemplary embodiment of the dome guide assembly according to the subject disclosure. The dome guide assembly 328 includes a hemi-spherical dome 330. The hemi-spherical dome 330 is constructed as a truncated hemisphere or frustum-like sphere having a hemi-spherical like circumferential wall 331 and a planar upper surface 333. The dome guide assembly 328 further includes a sphere-like or spherical-like centering body (or, simply, body) 332 extending distally from the hemi-spherical dome 330 which is sized and shaped to be received within an acetabular implant similar to the manner shown in FIG. 21. The sphere-like centering body 332 may be permanently attached to the hemi-spherical dome 330 or is detachably connected to the hemi-spherical dome such that sphere-like centering bodies of different size and shape may be attached to fit into implant liners of varying size and shape.

Figure 26:
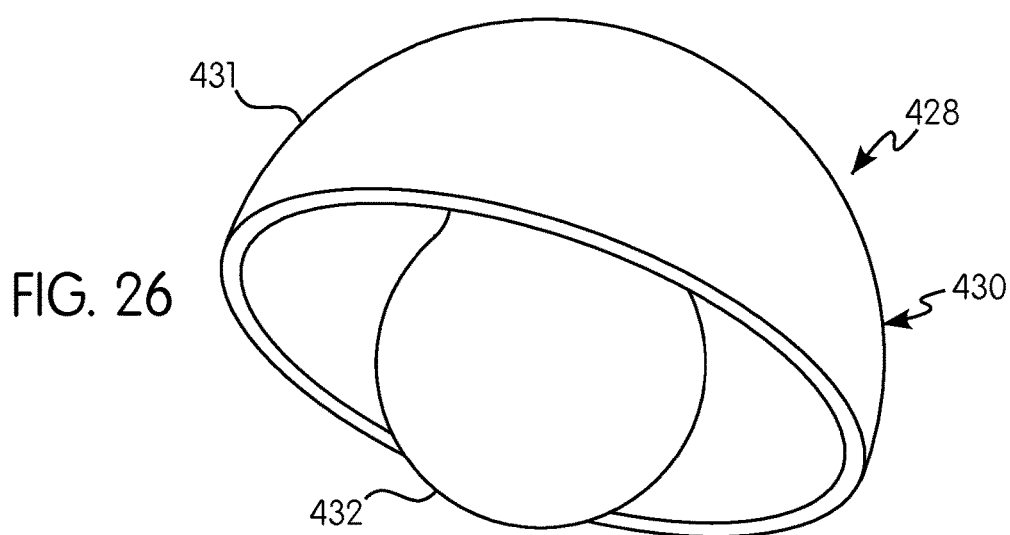
FIG. 26 is a bottom perspective view of another exemplary dome guide for use in the acetabular cup extractor system of FIG. 20.
Figure 27:
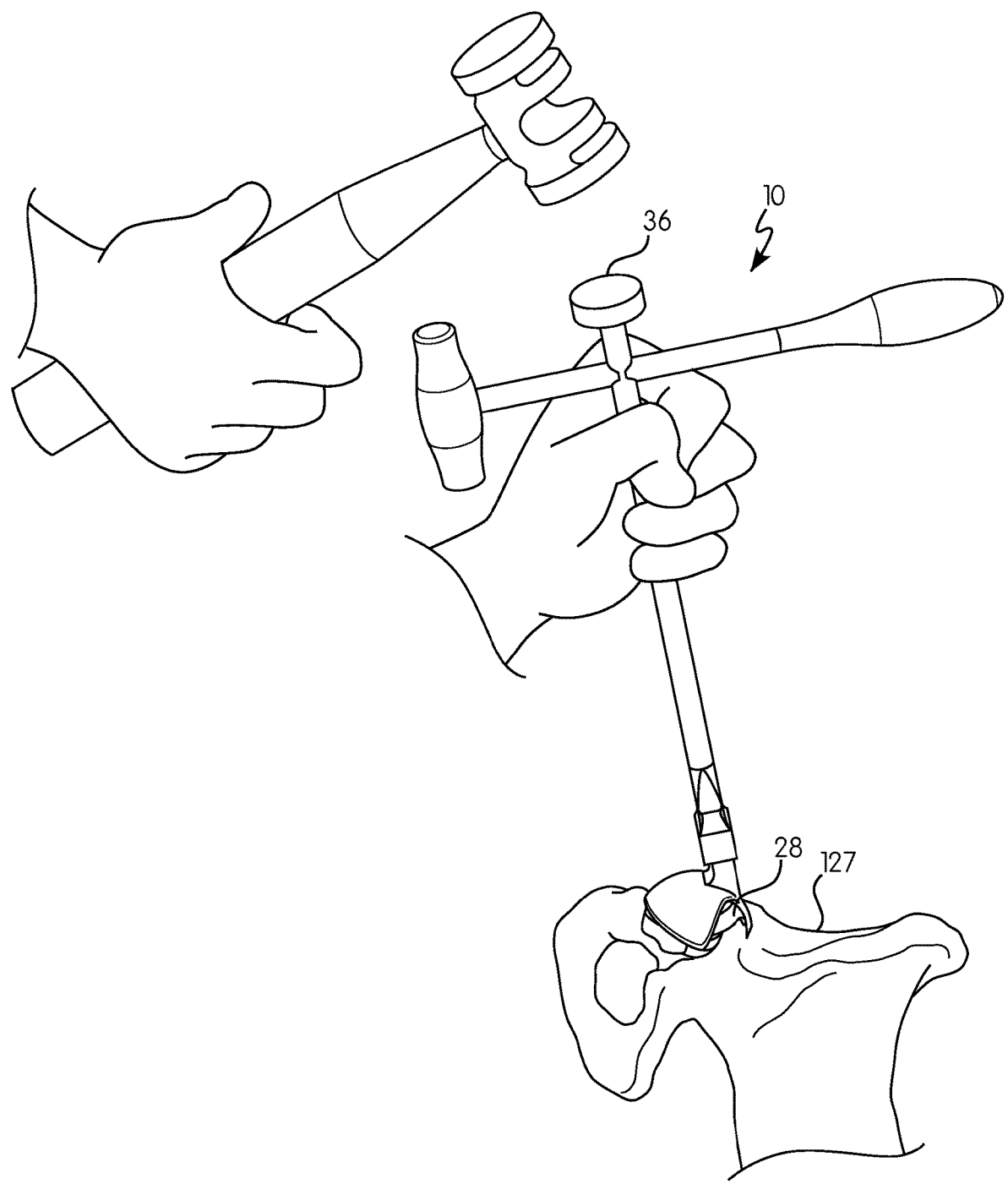
FIG. 27 is a perspective view of the acetabular cup extractor system of FIG. 1 mounted to an implant in an acetabulum.

Referring to FIG. 26, there is illustrated yet another exemplary embodiment of a dome guide assembly according to the subject disclosure. The dome guide assembly 428 includes a hemi-spherical dome 430. The hemi-spherical dome 430 is constructed as a substantially full hemisphere having a hemi-spherical circumferential wall 431.

The dome guide assembly 428 further comprises a sphere-like or spherical-like centering body (or, simply, body) 432 extending distally from the hemi-spherical dome 430 which is sized and shaped to be received within an acetabular implant similar to the manner shown in FIG. 21. The sphere-like centering body 432 may be permanently attached to the hemi-spherical dome 430 or is detachably connected to the hemi-spherical dome such that sphere-like centering bodies of different size and shape may be deployed to fit into implant liners of varying size and shape.

The dome guide assemblies 328 and 428 may be arranged as a kit. The kit may include a plurality of spherical-like centering bodies and hemi-spherical dome assemblies of different sizes, e.g., overall widths that match different sizes of various acetabular implant and implant liner sizes. Plus, the acetabular cup extractor system 210 may include extractors 222 of varying sizes, e.g., a plurality of extractors of varying size to accommodate implants of varying size.

In operation of the acetabular cup extractor system of the subject disclosure, the spherical-like centering body 32 with an appropriately sized and shaped sphere-like body 94 is selected and attached to the hemi-spherical dome assembly 30. It is understood that the hemi-spherical dome assembly 30 is likewise selected such that the spaced apart legs 92 of the circular mount 70 are of an appropriate diameter to substantially rest atop the periphery of an acetabular cup implant to be extracted. The extractor 22 is attached to the handle assembly at fastener 52. The sphere-like body 94 is then placed into engaging contact with an acetabular cup implant liner such as liner 86 (FIG. 28). Thereafter, the guide 24 of the extractor 22 is brought into mating engaging contact with the hemi-spherical dome assembly 30, in particular, the dome-like cap 72.

The point 66 of the extractor blade 26 is then torqued to pivot about the dome guide assembly 28 to force the point to cut into bone 127 (FIG. 28) surrounding the acetabular cup implant to be extracted. This movement causes the blade to cut into bone substantially the length of the blade 26. Alternatively, the user can strike the strike plate 36 of the handle if necessary to drive the point 66 and lateral cutting edges of the blade into the bone. The mating engaging shapes of the hemi-spherical shell-like guide 24 and the hemi-spherical dome assembly 30, in combination with the placement of the longitudinal shaft of the handle about the arc of the hemi-spherical shell-like guide 24, assures that the extractor 22 remains in stable contact with the hemi-spherical dome assembly 30 during use. The user then extracts the blade 26, which is a starter cutting blade, from the bone. If the blade 26 is stuck in the bone, the user can strike the planar undersurface 50 of second gripping handle 42 or the lower surface of the first gripping handle 38 to free the stuck blade from the bone. Once the blade 26 is extracted from the bone, the user rotates the handle 12 a desired angular distance and again places the point 66 of the blade 26 into contact with bone surrounding the acetabular cup implant to be extracted. The user then torques the handle or strikes the strike plate 36, thereby again driving the blade 26 into the bone. The user then extracts the blade from the bone, if need be by striking the flat surface 50 of second gripping handle 42 or the lower surface of the first gripping member 38 to free the blade from the bone. The foregoing process is repeated until a desired number of bone penetrations are achieved by the blade 26, such that sufficient bone is removed from contact with the implant to achieve removal.

Additionally, if implant removal with the starter blade 26 is not sufficient then the finishing blade 126 can be used to cut more/additional bone a deeper depth than the starter blade 26. In this regard, the user detaches the extractor 22 from the handle by depressing button 62 to disengage the detents 54, 56 and the hub or mount 64. Once the detents 54, 56 are disengaged, the user pulls the extractor 22 from the fastener 52. The user then attaches the second extractor 122 including the blade 126 to the fastener 52 by pushing the hub or mount 164 of the second extractor toward the fastener 52. In so doing, the detents of the of the sliding latch member 58 and the hub or mount 164 of the second extractor 122 come into mating engagement under the influence of biasing member 60 in the manner shown on FIG. 5.

The second extractor 122 is then used to continue the acetabular cup implant extraction process. The user inserts the blade 126 of the second extractor 122 into a hole previously cut into the bone 127 by the blade 26. The user can then torque by hand or strike the strike plate 36 thereby driving the blade 126 further beneath the acetabular cup implant to be extracted. Indeed, the longitudinal dimension of the blade 126 is capable of extending to substantially a bottom portion of the acetabular cup implant to be extracted when fully inserted into the surrounding bone. The user then extracts the blade 126, if need be by striking the undersurface 39 of the first gripping handle 38 or the flat surface 50 of second grip member 42 to free the blade from the bone. The user then inserts the blade 126 into another hole previously cut into the bone by the blade 26 and strikes the strike plate 36 of the handle to drive the blade 126 deep beneath the acetabular cup implant to be extracted. The blade 126 is then extracted as described and the process is repeated as necessary to remove the implant. The user can also exert a twisting force on the second gripping handle 42 of the handle 12 whereby the lateral cutting edges of the blade 126 cut bone that may be remaining between the puncture holes cut by the blade 26 and/or the blade 126 to form a continuous substantially hemi-spherically shaped cut adjacent to the acetabular cup implant. Thereafter, the user may tilt the handle 12 away from his or her body thereby causing the blade 126 to lift the acetabular cup implant from the surrounding cut bone.

Alternatively, the blade 126 may be used as the initial blade instead of or without the blade 26. The acetabular cup extraction process achievable by the extractor 222 and either of the dome guide assembly 328 or the dome guide assembly 428 is substantially similar to that associated with the extractors 22, 122 and dome guide assembly 28.

In accordance with the exemplary embodiments, there is provided an orthopedic instrument in the form of an acetabular cup extractor system for reliably and efficiently extracting an acetabular cup implant from an acetabulum. Among other things, the acetabular cup extractor system includes a tool in the form of a handle assembly, another tool in the form of an extractor at a distal end of the handle assembly, and a dome guide assembly having a hemi-spherical dome for engaging the extractor and a centering body extending distally from the hemi-spherical dome for engaging an acetabular implant. The extractor includes a curved, concave guide and a curved blade. The curved, concave guide is sized and shaped to substantially matingly engage with and cover a substantial portion of the hemi-spherical dome. In this way, when a user strikes the handle assembly with a hammer or similar tool, the downwardly directed impact force transferred by the handle assembly causes the mating engagement surfaces of the curved, concave guide and the hemi-spherical dome to remain in contact with each other, and the centering body and the acetabular implant to remain in contact with each other, as the curved blade is driven into the bone surrounding the acetabular cup implant. As a result, a uniform cut is achieved by the curved blade thereby resulting in a minimum of bone being extracted from the acetabulum around the acetabular cup implant during the surgical procedure.

The acetabular cup extractor system further includes a push-to connect fastener or chuck for releasably attaching the extractor to the blade.

The acetabular cup extractor system of the subject disclosure has a counter torque handle or transverse handle assembly including first and second gripping handles that enable a user to apply more lateral cutting torque to bone surrounding the acetabular cup implant. The torque handle is ergonomically shaped and substantially balanced making it easier for a user to apply cutting torque. The first and second gripping handles have impact surfaces that may be struck by a tool to allow easy dislodging of the blade when it becomes lodged in bone.

The present acetabular cup extractor system includes pointed blades the more easily penetrate bone.

Figure 29:
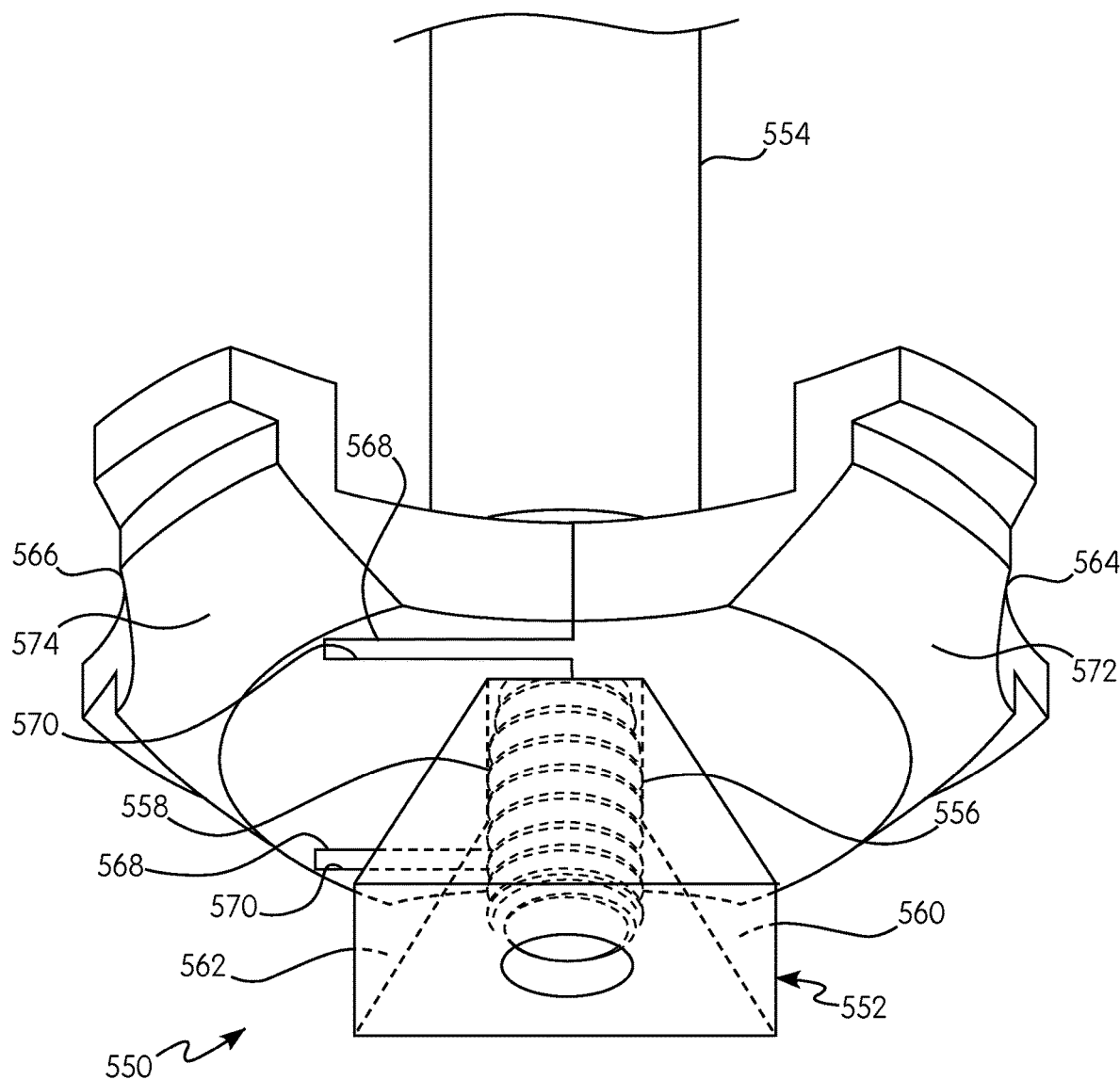
FIG. 29 is a bottom perspective view of an exemplary embodiment of an expandable centering device applicable to the acetabular cup extractor system in accordance with the subject disclosure.

In addition, the present acetabular cup extractor system may include an expanding centering device 550 that allows the dome guide assembly to accommodate implant liners of varying sizes or that are damaged. FIG. 29 illustrates an exemplary embodiment of the expanding centering device 550. The expanding centering device 550 comprises a wedge member 552 and a shaft 554. The wedge member 552 is internally threaded at 556 to receive a threaded portion 558 at a distal end of the shaft 554. Rotation of shaft 554 in a first direction causes threading 558 to engage threading 556 which raises the wedge member 552 relative to the shaft 554. In so doing, opposed sloped surfaces 560, 562 of wedge member 552 move upwardly to press against and spread apart opposed, translatable acetabular cup implant liner engagement members 564, 566. In order to assure even spreading of thereof, the acetabular cup implant liner engagement members 564, 566 are desirably provided with keys 568 provided on one of the acetabular cup implant liner engagement members 564, 566 which are matingly received in slots 570 provided in the other of the acetabular cup implant liner engagement members 564, 566. When the acetabular cup implant liner engagement members 564, 566 are sufficiently spread apart, outer sloped surfaces 572, 574 of the acetabular cup implant liner engagement members frictionally engage an inner surface of an implant liner such as liner 86 (FIG. 28). The shaft 554 may be provided with threading at its proximal end (not illustrated) similar to threading 80 of the spherical-like centering body 32 (FIGS. 16 and 17) for threading into to the mount 70 (FIGS. 12-14) of dome guide assembly 28. Consequently, the dome guide assembly, when attached to the expanding centering device 550, may be firmly anchored to the implant liner even if the liner is damaged.

It will be appreciated by those skilled in the art that changes could be made to the exemplary embodiments described above without departing from the broad inventive concept thereof. It is to be understood, therefore, that this disclosure is not limited to the particular exemplary embodiments disclosed, but it is intended to cover modifications within the spirit and scope of the subject disclosure as defined by the appended claims.

I claim:

1. An acetabular cup extractor system comprising:
   a handle including:
   an elongated shaft, and
   a transverse handle extending substantially transverse to a longitudinal axis of the elongated shaft;
   an extractor attachable to a distal end of the handle, the extractor including:
   a guide, and
   a blade; and
   a dome guide assembly that includes:
   a hemi-spherical dome for engaging the extractor, and
   a centering body extending distally from the hemi-spherical dome for engaging an acetabular implant.

2. The acetabular cup extractor system of claim 1, wherein the elongated shaft includes a strike plate about its proximal end.

3. The acetabular cup extractor system of claim 1, wherein the transverse handle includes a first gripping handle at a first end of the transverse handle and a second gripping handle at a second end of the transverse handle opposite the first end.

4. The acetabular cup extractor system of claim 3, wherein the first gripping handle has a longitudinal axis that extends transverse to a longitudinal axis of the second gripping handle.

5. The acetabular cup extractor system of claim 3, wherein the second gripping handle includes a planar strike plate.

6. The acetabular cup extractor system of claim 5, wherein the planar strike plate is a distally facing strike plate.

7. The acetabular cup extractor system of claim 3, wherein the first gripping handle has a longitudinal axis substantially parallel to a longitudinal axis of the elongated shaft.

8. The acetabular cup extractor system of claim 1, wherein the elongated shaft includes a fastener about its distal end for connecting to the extractor.

9. The acetabular cup extractor system of claim 1, wherein the guide is a curved guide, or a concave guide.

10. The acetabular cup extractor system of claim 1, wherein the blade is curved in both its longitudinal direction and in a widthwise extent transverse to the longitudinal direction.

11. The acetabular cup extractor system of claim 1, wherein a tangency of a surface of a base of the blade is at a non-zero angle relative to the longitudinal axis of the elongated shaft.

12. The acetabular cup extractor system of claim 1, wherein a portion of the blade extends beyond a plane defined by a side of the elongated shaft.

13. The acetabular cup extractor system of claim 1, wherein the extractor includes a mount for engaging a fastener of the elongated shaft.

14. The acetabular cup extractor system of claim 13, wherein the guide extends from the mount and the blade extends from the mount in a direction opposite the guide.

15. The acetabular cup extractor system of claim 1, wherein the hemi-spherical dome includes:
   a circular mount, and
   a dome-like cap mounted to the circular mount.

16. The acetabular cup extractor system of claim 15, wherein the circular mount includes a post and the dome-like cap includes a through hole for receiving the post.

17. The acetabular cup extractor system of claim 16, wherein the post includes a fastener for connecting with the centering body, or wherein an overall height of the dome-like cap is greater than an overall height of the post.

18. The acetabular cup extractor system of claim 15, wherein the dome-like cap has an overall width greater than an overall width of the circular mount.

19. The acetabular cup extractor system of claim 15, wherein the dome-like cap is polymeric, or metallic with a low-friction coating.

20. The acetabular cup extractor system of claim 1, wherein the centering body includes:
   a sphere-like body; and
   a fastener extending from the sphere-like body for connecting with the hemi-spherical dome.

21. The acetabular cup extractor system of claim 1, wherein the centering body includes a pair of flats at its lateral sides.

22. The acetabular cup extractor system of claim 1, further comprising a second extractor attachable to the distal end of the handle assembly, the second extractor including:
   a finishing guide, and
   a finishing blade having an overall length greater than the blade of the extractor.

\* \* \* \* \*